(12) United States Patent
Kawate

(10) Patent No.: US 7,649,633 B2
(45) Date of Patent: Jan. 19, 2010

(54) METHOD AND INSTRUMENT FOR MEASURING COMPLEX DIELECTRIC CONSTANT OF A SAMPLE BY OPTICAL SPECTRAL MEASUREMENT

(75) Inventor: Etsuo Kawate, Ibaraki (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 148 days.

(21) Appl. No.: 10/579,781

(22) PCT Filed: Nov. 22, 2004

(86) PCT No.: PCT/JP2004/017361

§ 371 (c)(1),
(2), (4) Date: Jan. 31, 2007

(87) PCT Pub. No.: WO2005/050177

PCT Pub. Date: Jun. 2, 2005

(65) Prior Publication Data

US 2008/0013070 A1    Jan. 17, 2008

(30) Foreign Application Priority Data

Nov. 20, 2003  (JP)  ............................ 2003-391201
Oct. 26, 2004  (JP)  ............................ 2004-311458

(51) Int. Cl.
  *G01B 11/02*  (2006.01)
(52) U.S. Cl. ...................................... 356/504; 356/51
(58) Field of Classification Search .................. 356/51, 356/364–369, 438, 504, 625, 630, 632
  See application file for complete search history.

(56) References Cited

U.S. PATENT DOCUMENTS 3,985,447 A  * 10/1976  Aspnes ..................... 356/369
5,500,599 A  *  3/1996  Stange ...................... 324/634

(Continued)

FOREIGN PATENT DOCUMENTS

JP          5-315307          11/1993

(Continued)

OTHER PUBLICATIONS

*Functional Material*, vol. 18, No. 10, 1998, p. 47.

(Continued)

*Primary Examiner*—Tarifur Chowdhury
*Assistant Examiner*—Michael Lapage
(74) *Attorney, Agent, or Firm*—Morgan Lewis & Bockius LLP

(57) ABSTRACT

In order to measure a complex dielectric constant of a thin film on a substrate, a method includes irradiating the thin film sample with light at a first incident angle so that the light undergoes multiple internal reflections within the thin film sample. The method also includes measuring light that has transmitted through or reflected on the thin film sample following the multiple internal reflections, and determining a complex dielectric constant of the thin film sample based upon a spectrum of the transmitted or reflected light that has undergone the multiple internal reflections.

9 Claims, 16 Drawing Sheets

U.S. PATENT DOCUMENTS

| | | | |
|---|---|---|---|
| 5,991,488 A | * | 11/1999 | Salamon et al. ............. 385/129 |
| 2001/0029436 A1 | | 10/2001 | Fukasawa |
| 2003/0016358 A1 | | 1/2003 | Nagashima et al. |
| 2004/0008346 A1 | | 1/2004 | Kawate |
| 2004/0169863 A1 | | 9/2004 | Kawate |

FOREIGN PATENT DOCUMENTS

| | | |
|---|---|---|
| JP | 8-216016 | 8/1996 |
| JP | 10-281710 | 10/1998 |
| JP | 11-166952 | 6/1999 |
| JP | 2000-193608 | 7/2000 |
| JP | 2002-98634 | 4/2002 |
| JP | 2002-214161 | 7/2002 |
| JP | 2002-228600 | 8/2002 |
| JP | 2002-286771 | 10/2002 |
| JP | 2003-14620 | 1/2003 |
| JP | 2004-247956 | 9/2004 |
| WO | 01/65239 | 9/2001 |
| WO | 02/95372 | 11/2002 |

OTHER PUBLICATIONS

Osamu Hashimoto et al., "Measurement of Complex Permittivity of Radardome Material at 60 GHz Frequency Band," The Institute of Electronics, Information and Communication Engineers, Paper, B-II, vol. J80-B-II, No. 10, 1997, p. 906.

Kunio Fujisawa et al., *Optics/Electro-optics II*, Akasura Physics Course 12, Akasura Bookstore, 1965, pp. 138-156.

M. Li, et al.: "Time-domain dielectric constant measurement of thin film in GHz-THz frequency range near the Brewster angle" Applied Physics Letters, vol. 74, No. 15, Apr. 12, 1999, pp. 2113-2115.

Kawate, et al. "Determination of dielectric constant of a thin and low-dielectric film in the millimeter wave region", Applied Physics Letter, vol. 84, No. 24, May 25, 2004, pp. 4878-4880.

Stephen E. Ralph et al., "Terahertz Spectroscopy of Optically Thick Multilayered Semiconductor Structures," *Journal of the Optical Society of America*, vol. 11, No. 12, Dec. 12, 1994, pp. 2528-2532.

Etsuo Kawate et al., "Expanding Optical Measurement Methods of Thin Films in the Far-infrared Towards the Lower Frequency Region," *THz 2003 Technical Digest*, 11th International Conference on Terahertz Electronics, p. 129, Sep. 2003.

* cited by examiner

FIG. 1 (a) PRIOR ART
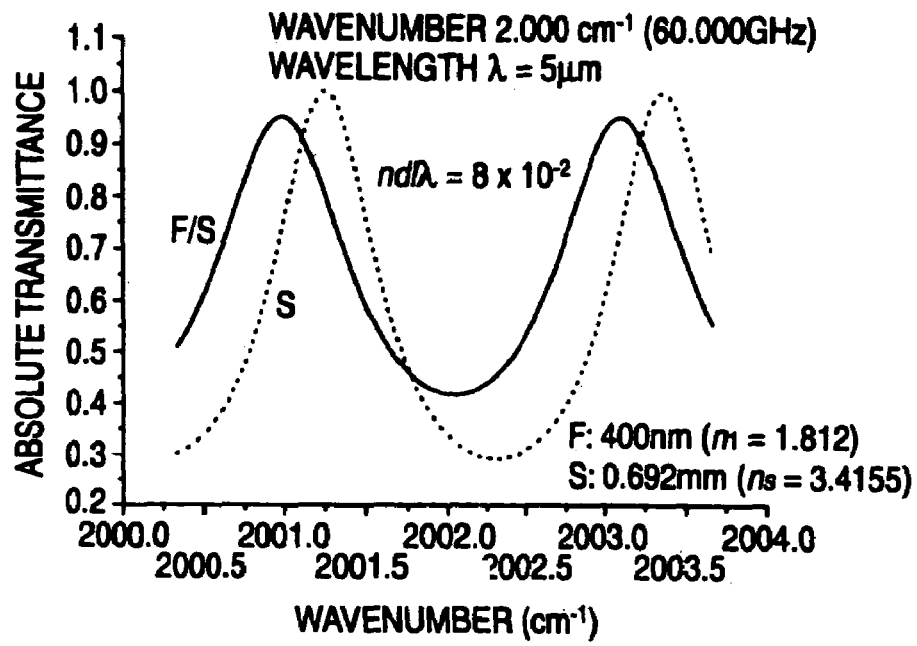
FIG. 1 (b) PRIOR ART
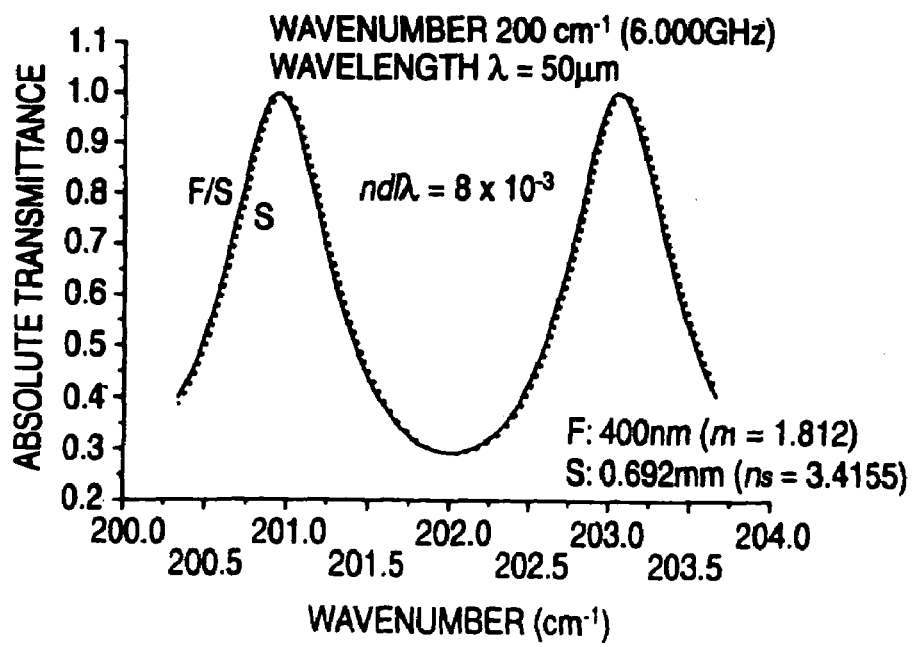

FIG. 1 (c) PRIOR ART
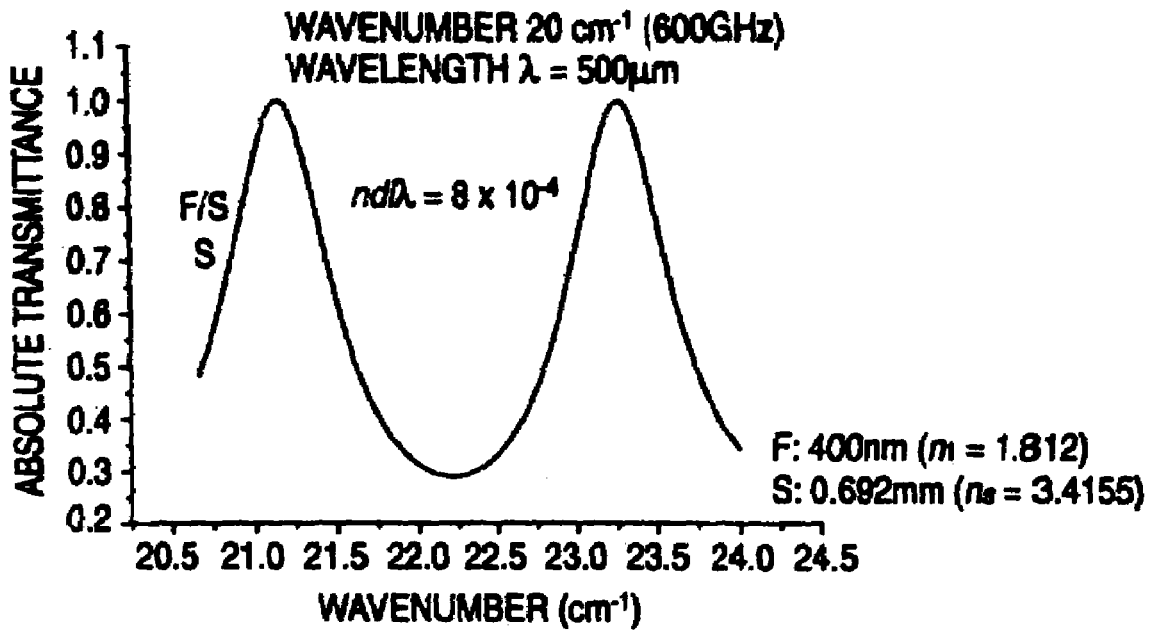
FIG. 1 (d) PRIOR ART
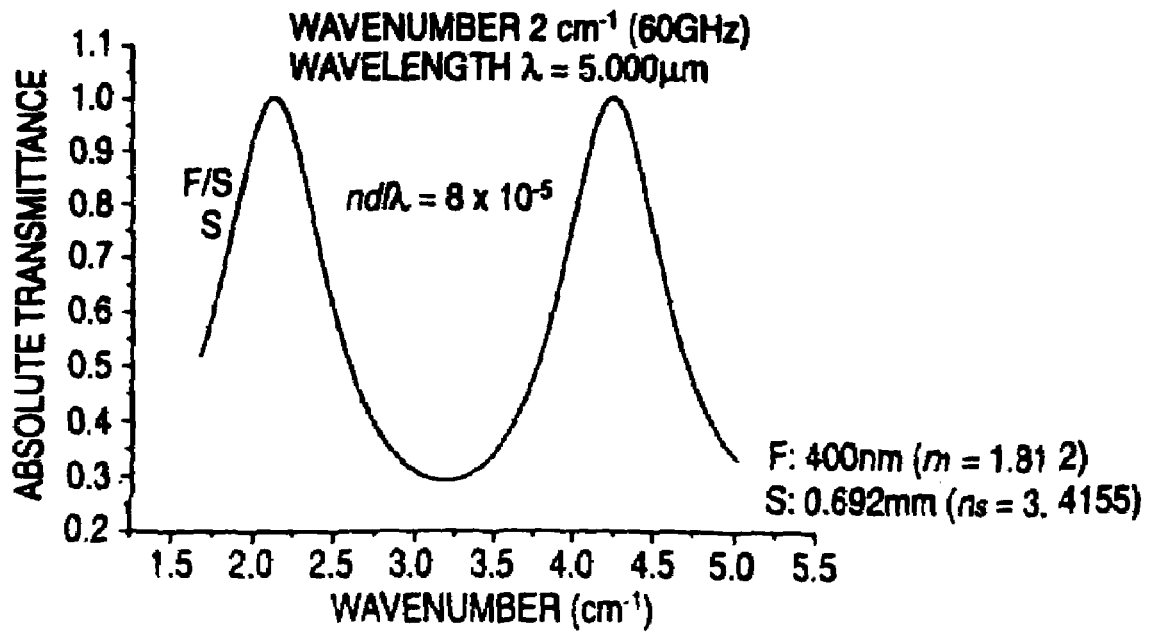

METHOD AND INSTRUMENT FOR MEASURING COMPLEX DIELECTRIC CONSTANT OF A SAMPLE BY OPTICAL SPECTRAL MEASUREMENT

TECHNICAL FIELD

The present application is a U.S. National Stage Entry of International Application No. PCT/JP04/17361 filed on Nov. 22, 2004 and claims the benefit of Japanese Patent Applications No. 2003-391201 filed on Nov. 20, 2003 and No. 2004-311458 filed on Oct. 26, 2004, which are both hereby incorporated by reference.

The present invention relates to an apparatus and method for measuring a complex dielectric constant of a thin film on a substrate, based on a measurement of a change in spectra of light irradiated on a substrate and a thin film on the substrate.

BACKGROUND ART

In the capacitive method, which is based on the capacitance measurement of a capacitor, a complex dielectric constant of a thin film on a substrate can be measured by use of an LCR meter in the range of several GHz or lower (see "Patent Document 1" below, for example). The measurement limit on the high-frequency side is caused by a difficulty in correcting the effect of electrode loss and LC resonance caused by electrode inductance.

It is a general practice to use a resonator method in measuring a complex dielectric constant in the high frequency range. The complex dielectric constant of a thin film on a substrate can be determined by measuring a change in intensity and phase with respect to a propagating direction by use of a network analyzer on a strip line, micro-strip line, etc. constituted by its thin film and electrodes (see "Patent Document 2" below, for example). This method allows for measuring a complex dielectric constant in the range of 0.1 GHz-10 GHz. In this case, the measurement limit on the high-frequency side is determined by a fact that it is difficult to obtain the characteristic of the thin film only. That is, it is difficult to completely separate and remove the loss in the conductor configuring the line from the measurement.

In order to measure a complex dielectric constant of a thin film on a substrate in a higher frequency range, the cavity resonator method is used. Resonant frequency, Q value, etc. are measured by a network analyzer in the presence and in the absence of an on-substrate-film sample inserted in the cavity resonator to thereby determine a complex dielectric constant of the thin film (see "Patent Document 3" below, for example). With this method, measurement is feasible for a complex dielectric constant in the range of 1 GHz-50 GHz. The measurement limit on the high-frequency side, in this case, is determined by the physical size of the cavity resonator. Namely, the cavity resonator has dimensions that approximate the wavelength (approximately 6 mm at 50 GHz), in which case the dimensional accuracy of the cavity resonator is based on the fabrication accuracy in manufacturing the resonator. That is, if the dimensional accuracy is low, there are greater errors in measurement.

The capacitive and resonance methods are destructive measurements that require working on the measuring sample to be inserted, in order to match the dimensions to the measuring tool. However, this requires a considerable labor and cost. Meanwhile, where the exterior dimensions, particularly in a part contacting with the inner wall of the measuring tool, of a sample have low accuracy, significant errors of measurement occur thus making it difficult to implement a correct measurement.

There are two non-destructive measuring methods that do not require working on the sample to measure. One is a method to clamp a sample between waveguides, and the other is to irradiate a sample with light.

By clamping a sample between two waveguides, a network analyzer can measure a reflection coefficient at one aperture and a transmission coefficient at the other aperture. The absolute value and phase angle of these coefficients are substituted in a simultaneous equation deduced by resolving the Maxwell equation, thereby determining a complex dielectric constant of the thin film on the substrate (see "Patent Document 4" below, for example). This method, called a non-resonant technique, is of a non-destructive measurement. This method allows for measuring a complex dielectric constant in the range of 1 GHz-100 GHz (approximately 3 mm in wavelength). The measurement limit on the high-frequency side is determined by the fabrication accuracy of the waveguides, which is similar to the foregoing paragraphs [0004] and [0005].

For measuring a complex dielectric constant, there is an "optical measuring method" in the direction from higher frequency to lower frequency, which is separate from the "electric measuring method" in the direction from lower frequency to higher frequency. In the optical measurement technique, generally a complex dielectric constant-can be measured under atmospheric pressure without destruction of and contact with the sample. These optical measurement methods are called free space techniques.

In the method of determining a complex dielectric constant from an optical response (reflection or transmission light) when a sample is irradiated with light, the complex dielectric constant becomes difficult to measure as the ratio $nd/\lambda$ becomes smaller provided that the sample has a thickness of d and a refractive index of n wherein a measuring wavelength is $\lambda$. This is because light is a wave that travels by repeating the wave "crest" and "root". When the sample is thin, e.g. $nd/\lambda=0.001$ or around, the sample interacts with just a part between the "crest" and the "root" of the incident light so that it seems that a direct-current electric field is applied to the sample. That is, the capacitor on a direct current is a mere insulator wherein the complex dielectric constant approximates to a real constant. For the above reason, when the ratio $nd/\lambda$ is small, there is a difficulty in measuring a complex dielectric constant.

When a complex dielectric constant of a thin film is determined by irradiating a transparent sample with light and measuring a transmission spectrum thereof, measurement becomes difficult as the thickness of the thin-film decreases and the measurement wavelength increases. The computation result of this situation is shown in FIG. 1. The results shown here are the computation results of transmittance spectra where the measurement wavelength is changed, and the sample thickness and complex dielectric constant fixed. A thickness and refractive index of the substrate (S) are 700 μm and 3.4155, respectively, while a thickness and refractive index of the thin film (F) are 0.4 μm and 1.812, respectively. In the figures, the solid line is a transmittance spectrum (T(F/S)) of a sample formed of a thin film on a substrate, while the dotted line is a transmittance spectrum (T(S)) of the substrate only. In the figures, the spectra are depicted for approximately two fringes.

In FIG. 1(a), the incident wavelength is about 5 μm (middle infrared ray) to have $nd/\lambda=0.14$; in FIGS. 1(b)-1(d), the wavelength is increased one order per each figure. In FIG. 1(d), the wavelength is about 5 mm (about 60 GHz in frequency), and nd/λ=0.00014. In FIGS. 1(c) and 1(d), there is substantially no difference between the transmittance spectrum (T(S)) through only the substrate and the transmittance spectrum (T(F/S)) through the thin film on the substrate, in which state there is quite a difficulty in determining a complex dielectric constant of the 0.4-μm thin film. Here, complex dielectric constant (∈) and complex refractive index (n) are held with a relationship of "a square of n equals ∈ ($n^2$=∈)". Refractive index, without "complex," means a real part of the complex refractive index.

The free space method includes an approach to directly measure an amplitude and phase of a reflection coefficient at a fixed incident angle (see "Non-Patent Document 1" below, for example) and approaches to determine a complex dielectric constant from a dependence of reflectance upon incident angle, and a dependence of reflectance upon sample thickness and a dependence of reflectance upon frequency (see "Non-Patent Document 2" below, for example). In the measurement at a fixed incident angle, an expensive measuring apparatus such as a network analyzer is required to measure an amplitude and phase of the reflection coefficient. In the method in which the incident angle is changed, there is no need for a network analyzer because merely an energy reflectance is measured. However, it is common for both measurements to measure an absolute reflectance. This requires a metal plate equal in size to the sample as a reference sample. In a case where the metal plate is not provided in the same size and set-up position as the sample-to-measure, there arises a measurement error problem.

There is a new reflectance measurement method that does not require a metal reference sample. This is a method for determining a complex dielectric constant from a ratio of a TE-wave reflection coefficient to a TM-wave reflection coefficient of a sample irradiated with a circular-polarization electromagnetic wave in a millimeter-wave band (see "Patent Document 5" below, for example).

In the measurement using the free space method, sensitivity is generally low. As for the best data so far, complex dielectric constant is determined by irradiating a 925-GHz (λ=324 μm) sub-millimeter wave at a changing incident angle to a low-dielectric (Low-k) polymer thin film (n=1.7), which has a thickness d=3.27 μm on a silicon substrate and then measuring a reflectance at around a Brewster's angle (see "Non-Patent Document 3" below, for example). The value nd/λ in this case is 0.02.

As described above, in either an electric measurement or an optical measurement, it is generally difficult to measure a complex dielectric constant of a thin film on a substrate at a frequency in the range of 30 GHz-3 THz (100 μm-10 mm, in wavelength).

The frequency band, used today in communication systems, includes sub-microwave bands of 1.9 GHz and 2.45 GHz and a sub-millimeter band of 19 GHz. The sub-microwave band is assigned to the personal handy phone system (PHS) and the medium-speed wireless LAN internal radio device. Meanwhile, the sub-millimeter-wave band is assigned to the high-speed wireless LAN internal radio device.

Furthermore, development in the future is expected for the higher frequency range of 30 GHz-3 THz. Research and development is active for a codeless communication system in a 50 GHz band and a collision-prevention vehicular radar and ultra high-speed wireless LAN in 60 and 70 GHz bands. Thus, a drastic progress is expected for the information communication technology. Furthermore, in the higher frequency range, practical applications at present are made in the millimeter/sub-millimeter wave astronomy and nuclear-fusion plasma research and development. Thus, the higher frequency range plays an important role. In order to develop a new device for use in the higher frequency range, it is essential to measure a complex dielectric constant of the existing and novel substances in the higher frequency range, which is important technology.

Due to the increase in integration and miniaturization of the devices in the semiconductor industries, the quality of semiconductor wafers is strictly required. Particularly, high flatness is required for a semiconductor wafer used as a substrate. The requirement has been satisfied each time by the conspicuous advancement of polish technology.

However, in order to improve flatness, there is a need for, in addition to polish technology, an accurate method and device for measuring flatness in order to evaluate the semiconductor wafer. The capacitive method and the optical interference method are the methods that are broadly used in measuring a thickness of a product semiconductor. These methods are capable of non-contact evaluation of a flatness of the entire surface of a wafer.

In the capacitive method, a sample is inserted between two opposite electrodes (parallel-plate capacitor) to thereby detect a capacitance change and hence measure a sample local thickness. The sample surface is scanned by the capacitor to determine a flatness of the entire surface (see "Patent Document 6", for example). The capacitive method is advantageous because it is affected less by particles compared to optical-interference-scheme flatness measurement. Furthermore, the capacitive method can measure a thickness and flatness of a wafer of the type ranging from a slice wafer to a wafer with a pattern in the non-contact manner. However, this method requires applying a surface active agent solution to a semiconductor wafer surface. Furthermore, pre-processing is required to remove a native oxide film existing in the semiconductor wafer surface.

In the interference method, a semiconductor wafer is irradiated with an infrared ray and the reflection light from the sample is converted into an electric signal by a photodetector. In the spectrum measured, there appear fringes resulting from multi-reflection within the semiconductor wafer. A local thickness of the sample is determined from the interval of the fringes. The light irradiation point is scanned over the sample surface, to determine a flatness over the entire surface (see "Patent Document 7" below, for example). This process does not require a pre-processing and in-situ measurement is available during a polish process.

Today, in practical application a flatness of 1-5 μm can be achieved by a polish process (see "Patent Document 7" below, for example). In a case where a substrate surface form before polishing is measured by a flat measurer, and the substrate is deformed while being vacuum-absorbed by a rectification chuck and rectified into a desired form on the basis of the measurement result so that the polish keeps the rectified form, then a flatness of 0.3 μm can be achieved (see "Patent Document 8" below, for example).

[Patent Document 1] JP-A-2002-286771
[Patent Document 2] JP-A-11-166952
[Patent Document 3] JP-A-2002-228600
[Patent Document 4] JP-A-2002-214161
[Patent Document 5] JP-A-2000-193608
[Patent Document 6] JP-A-10-281710
[Patent Document 7] JP-A-8-216016
[Patent Document 8] JP-A-5-315307
[Non-patent document 1] Functional Material, Vol. 18, No. 10, (1998), p. 47

[Non-patent document 2] The Institute of Electronics, Information and Communication Engineers, Paper, B-II, Vol. J80-BII, No 10, (1997), p. 906

[Non-patent Document 3] Applied Physics Letter vol. 74, (1999), 2113-2115

[Non-patent Document 4] Optics/Electro-optics II, Authors: Kunio Fujiwara, Sigeo Yamaguchi (Asakura Physics Course 12, Asakura Bookstore), p 138-156.

DISCLOSURE OF THE INVENTION

[Problem that the Invention is to Solve]

The present invention, made in view of the circumstance of the prior art, aims at a technical development for measuring a complex dielectric constant of a thin film on a substrate from the fact that the product development in the future is moving toward a frequency higher than 30 GHz. There is a great demand for measuring a complex dielectric constant of a Low-k (low dielectric: explained later) thin film on a substrate in that frequency range, practical application is possible as an apparatus for in-situ product control at a semiconductor-industry manufacturing site provided that there is a technique capable of measuring a complex dielectric constant in that frequency range even if the thin film has a thickness of 1 μm or smaller. However, because the semiconductor wafer practically used in the semiconductor industry has a flatness greater than 1 μm, the foregoing target could not be achieved by the development of a mere high-sensitivity, conventional complex-dielectric-constant measuring apparatus. In the invention, it is an object of the invention to solve a technical object by providing a method and apparatus capable of measuring a complex dielectric constant even if the thin film has a thickness of 1 μm or smaller, by measuring both a substrate flatness and a on-substrate-film complex dielectric constant by the same measuring apparatus.

[Means for Solving the Problem]

From now on, paragraphs [0026] to [0033] describe means for resolution based on light transmission, while paragraphs [0034] to [0044] describe means for resolution based on light reflection.

<Transmission Case>

Transmittance measurement is possible at a wavelength at which the semiconductor substrate is transparent. Furthermore, where the substrate is a parallelepiped plate, a fringe appears in the transmission spectrum because of the multi-reflection at the interior of the substrate. As for the fringe of transmission spectrum, the frequency at which a spectral peak point is given (hereinafter, referred to as a "peak frequency") is expressed by:

$$v_s = \frac{cN}{2d_s\sqrt{n_s^2 - \sin^2\theta}} \quad \text{[Equation 1]}$$

where c and N are respectively the light velocity and an integer while $v_s$, $d_s$, $n_s$ and $\theta$ are respectively a peak frequency, a substrate thickness, a substrate refractive index and an incident angle. Similarly, a fringe appears in a transmission spectrum through the on-substrate thin film. The fringe has a peak frequency expressed by:

$$v_f = \frac{cN}{2d_s\sqrt{n_s^2 - \sin^2\theta} + 2d_f\sqrt{n_f^2 - \sin^2\theta}} \quad \text{[Equation 2]}$$

where $v_f$, $d_f$ and $n_f$ are respectively a peak frequency, a thin-film thickness and a thin-film refractive index.

The difference $\Delta v(=v_f-v_s)$ between the peak frequency for the substrate and the peak frequency for a sample where a thin film is formed on the substrate (hereinafter, referred to as a "peak frequency difference") is determined from (Equation 1) and (Equation 2), as in the following.

$$\frac{\Delta v}{v_s} \approx -\frac{d_f\sqrt{n_f^2 - \sin^2\theta}}{d_s\sqrt{n_s^2 - \sin^2\theta}} \quad \text{[Equation 3]}$$

Here, estimation is first made for the case of a high dielectric-constant thin film (High-k). In the case where the substrate is, for example, of silicon ($n_s$=3.4, $d_s$=700 μm) and the thin film (thickness $d_f$=1 μm) is of a High-k material such as a metal, then $n_f$ of about 100 or greater is feasible. At this time, the peak frequency difference Δv, in the time a millimeter wave at around 65 GHz is irradiated at a normal incidence, is determined as -2.7 GHz from (Equation 3). Meanwhile, from (Equation 1), the fringe peak frequency for the substrate is determined as 63 GHz. In the presence and absence of a High-k thin film, the peak frequency in one fringe shifts approximately 4% (=-2.7/63) toward the lower frequency. This is a quantity detectable by measuring a transmission spectrum on each sample. Thus, a complex dielectric constant of a 1-μm thick High-k thin film can be determined. In this connection, peak point in one fringe is shifted approximately 13% in FIG. 1(a) and approximately 1.5% in FIG. 1(b), toward the lower frequency.

Estimation is next made for a low dielectric (Low-k) film. In the case where the substrate is, say, of silicon ($n_s$=3.4, $d_s$=700 μm) and the thin film (thickness $d_f$=1 μm) is of a Low-k material such as a thermal oxide film ($SiO_2$) of silicon, the result is $n_f$=1.8. At this time, there is summarized, in Table 1, a determination result of a peak frequency difference Δv (Equation 3) when a millimeter wave at around 65 GHz is irradiated at a changing incidence angle and an in-fringe peak frequency $v_s$ (Equation 1) for the silicon substrate.

TABLE 1

| | 0 degree | 60 degrees | 70 degrees | 80 degrees | 85 degrees | 90 degrees |
|---|---|---|---|---|---|---|
| Δv (GHz) | -0.0492 | -0.0447 | -0.0436 | -0.0430 | -0.0428 | -0.0428 |
| $v_s$ (GHz) | 63.0252 | 65.1749 | 65.5796 | 65.8479 | 65.9182 | 65.9419 |
| Δv/$v_s$ (%) | -0.078 | -0.069 | -0.067 | -0.065 | -0.065 | -0.065 |

In the presence and absence of a Low-k thin film, the peak position shifts as little as approximately 0.078% (=Δv/$v_s$=-0.04916/63.02520) in maximum toward the lower frequency. For this reason, even in a case where transmission spectrum is measured on the sample, a peak frequency difference could not be detected. Hence, in this state, complex dielectric constant of the Low-k thin film could not be determined.

In the calculation of Table 1, because the silicon complex refractive index includes a finite value ($n_s$=3.4) in its real part and zero (k=0) in its imaginary part, the transmittance is 100% at the transmission peak. Furthermore, those on the third line ($v_s$) in Table 1 are the first-fringe peak frequencies (N=1) and also the interval of fringe peaks.

There is shown in FIG. 2 the dependences, upon incident angle, of S-polarization and P-polarization transmittances (Ts and Tp) and reflectances (Rs and Rp). Herein, they are the calculation results where a 60-GHz millimeter wave has been irradiated to a silicon substrate ($n_s$=3.4 and $d_s$=700 μm). With respect to the S-polarization transmittance (Ts), as the incident angle is increased, the transmittance begins decreasing at about 30 degrees and decreases in an accelerated manner at about 60 degrees, thus becoming zero at 90 degrees. As for the P-polarization transmittance (Tp), after taking the maximum value at the Brewster's angle of about 75 degrees, the transmittance monotonously decreases with the increasing incident angle, thus becoming zero at 90 degrees.

From paragraph [0029], at a peak frequency of a fringe appearing due to the multi-reflection at the interior of the substrate, transmittance takes the maximum value (transmittance of 100% at k=0) without relying upon the incident angle. Meanwhile, from paragraph [0030], at a frequency off the peak frequency, transmittance nears zero as the incident angle is increased. When those two effects are combined together, S-polarization transmission spectrum gradually narrows in its width-at-half-maximum with an increase in the incident angle, thus spectrum becoming sharp. This manner is shown in FIG. 3. At the incident angle exceeding 60 degrees, the degree of narrowing becomes conspicuous.

From those on the second line ($\Delta v$) in Table 1, there is a shift in transmittance-spectrum peak frequency of the substrate and of the on-substrate thin film. In a case where a substrate absolute transmission spectrum (T(S)) and an on-substrate-thin-film-sample absolute transmission spectrum (T(F/S)) are measured and a ratio of these transmission spectrums are determined (relative transmittance: T(F/S)/T(S)), a curve obtained is where the maximum and minimum values are adjacent. This manner is shown in FIGS. 4(a) and 4(b). In FIG. 4(a), there are transmission spectra for the on-substrate thin film (solid lines) and transmission spectra for the substrate (dotted lines), at incident angles of 0, 70 and 85 degrees. In FIG. 4(b), the curve where the maximum and minimum values are adjacent has a peak and valley in a height increasing with the increasing incident angle (oblique incidence) because of the effect described in paragraph [0031]. In this calculation, the substrate was silicon ($n_s$=3.4155+i0.001 and $d_s$=700 μm) while the thin film was silicon thermal oxide film ($n_f$=1.812+i0.001 and $d_f$=20 μm). With an incidence at an angle of 0 degrees upon a 20-μm thick thin-film sample on the substrate (700 μm), a peak appears having a maximum-to-minimum-value spacing of 20.5 GHz and a peak of 5%. At an incident angle of 70 degrees, the spacing between the maximum and minimum values is 4.45 GHz to have a peak of 18%. At an increased incident angle of 85 degrees, a peak of 70% appears with the spacing of the minimum and maximum values of 2.25 GHz. As apparent from FIGS. 4(a) and 4(b), the maximum-to-minimum-value spacing of a relative transmission spectrum, in transmission measurement, has a width nearly equal to a width-at-half-maximum of each absolute transmission spectrum.

When the substrate k is not zero, the transmittance spectra for the substrate and on-substrate thin film have their peaks decreasing from 100%. However, because the decrease is equal between the both, the ratio thereof (see paragraph [0030]) is qualitatively equal to FIGS. 4(a) and 4(b). Meanwhile, when the thin film k is not zero, the transmission spectrum for the on-substrate thin film has a peak lower than that of the substrate. As a result, in a case where a ratio in transmittance spectrum of the substrate and on-substrate thin film is determined, the maximum value decreases.

<Reflection Case>

With a substrate in the form of a parallelepiped plate, a fringe appears in its reflection spectrum due to the multi-reflection at the interior of the substrate. The frequency at which a fringe valley is given (hereinafter, referred to as a "valley frequency") is expressed as:

$$v_s = \frac{cN}{2d_s\sqrt{n_s^2 - \sin^2\theta}} \quad \text{[Equation 4]}$$

where c and N are respectively the light velocity and an integer while vs, ds, ns and θ are respectively a valley frequency, a substrate thickness, a substrate refractive index and an incident angle. Similarly, a fringe appears in the reflection spectrum for the on-substrate thin film sample, which fringe has a valley frequency expressed by:

$$v_f = \frac{cN}{2d_s\sqrt{n_s^2 - \sin^2\theta} + 2d_f\sqrt{n_f^2 - \sin^2\theta}} \quad \text{[Equation 5]}$$

where vf, df and nf are respectively a valley frequency, a thin-film thickness and a thin-film refractive index.

The difference $\Delta v$ (=vf−vs) between the valley frequency for the substrate and the peak frequency for the sample where a thin film is formed on the substrate (hereinafter, referred to as a "valley frequency difference") is determined from (Equation 4) and (Equation 5), as in the following.

$$\frac{\Delta v}{v_s} \approx -\frac{d_f\sqrt{n_f^2 - \sin^2\theta}}{d_s\sqrt{n_s^2 - \sin^2\theta}} \quad \text{[Equation 6]}$$

Here, estimation is first made as to the case of a high dielectric-constant thin film. In the case where the substrate is, say, of silicon (ns=3.4, ds=700 μm) and the thin film (thickness df=1 μm) is of a material high in dielectric constant such as a metal, then nf of about 100 or greater is feasible. At this time, the valley frequency difference, in the time a millimeter wave at around 65 GHz (λ=4,600 μm) is irradiated at a normal incidence, is determined as −2.7 GHz from (Equation 6). Meanwhile, from (Equation 4), the fringe valley frequency for the substrate is determined as 63 GHz. In the presence and absence of a high dielectric-constant thin film, the valley frequency in one fringe shifts approximately 4% (=−2.7/63) toward the lower frequency. This is a quantity detectable if reflection spectrum is measured on each sample. Thus, a complex dielectric constant of a 1-μm thick high dielectric-constant thin film can be determined. Here, nd/λ=0.02 is provided which is an intermediate value of between FIG. 1(a) and FIG. 1(b).

Estimation is next made for a low dielectric (Low-k) film. For instance, a Low-k material of which substrate is made of silicon (ns=3.4, ds=700 μm), and of which thin film (thickness df=1 μm) is made of a thermal oxide film (SiO$_2$) of silicon, the result is nf=1.8. At this time, there is summarized, in Table 2, a determination result of a valley frequency difference Δv (Equation 6) when a millimeter wave at around 65

GHz is irradiated while changing the incidence angle and an in-fringe valley frequency vs (Equation 4).

TABLE 2

|  | 0 degree | 60 degrees | 70 degrees | 80 degrees | 85 degrees | 90 degrees |
|---|---|---|---|---|---|---|
| $\Delta v$ (GHz) | −0.0492 | −0.0447 | −0.0436 | −0.0430 | −0.0428 | −0.0428 |
| $v_s$ (GHz) | 63.0252 | 65.1749 | 65.5796 | 65.8479 | 65.9182 | 65.9419 |
| $\Delta v/v_s$ (5) | −0.078 | −0.069 | −0.067 | −0.065 | −0.065 | −0.065 |

In the presence and absence of a Low-k thin film, the valley position shifts as little as approximately 0.078% (=$\Delta v/v_s$=−0.04916/63.02520) in maximum toward the lower frequency in one fringe. For this reason, even in a case were reflection spectrum is measured on the sample, a valley frequency difference could not be detected. Hence, in this state, the Low-k thin film could not be determined for complex dielectric constant.

In the calculation of Table 2, because the silicon complex refractive index is assumed a finite value (ns=3.4) in its real part and zero (k=0) in its imaginary part, the reflectance is 0% at the valley of the reflection spectrum. Furthermore, those on the third line (vs) in Table 2 are the first-fringe valley frequencies (N=1), which are also the interval of fringe valleys.

There is shown in FIG. 2 the dependences, upon incident angle, of S-polarization and P-polarization transmittances (Ts and Tp) and reflectances (Rs and Rp). Herein, those are a calculation result at 60 GHz lower than the valley frequency. With respect to the S-polarization reflectance (Rs), as the incident angle is increased, the reflectance begins increasing monotonously at from about 30 degrees and increases at an accelerated rate at about 60 degrees, then assuming 1 at 90 degrees. With respect to the P-polarization reflectance (Rp), after taking the minimum value at the Brewster's angle of about 75 degrees, the reflectance monotonously increases with the increasing incident angle, thus becoming 1 at 90 degrees.

From paragraph [0037], at a valley frequency of a fringe appearing due to the multi-reflection at the interior of the substrate, the reflectance takes a minimum value (reflectance of 0% at k=0) without relying upon the incident angle. Meanwhile, from paragraph [0038], at a frequency off the valley frequency, the reflectance nears 1 as the incident angle is increased. When those two effects are combined together, the reflection spectrum gradually narrows in its width-at-half-maximum with an increase in the incident angle, thus becoming a sharp spectrum. This manner is shown in FIG. 5. In the figure, plotting is made as to a reflection spectrum, against frequency, at an incident angle of 0 degree (solid diamond), 60 degrees (solid triangle), 70 degrees (solid circle), 80 degrees (solid square) and 85 degrees (solid line). In a case where the incident angle exceeds 60 degrees, the degree of narrowing becomes conspicuous.

From those on the second line ($\Delta v$) in Table 2 of paragraph [0037], there is a shift in the valley frequency of reflection spectrum for the substrate and the on-substrate thin film. In a case where an absolute reflectance spectrum (R(S)) of the substrate, and that of an on-substrate-thin film-sample (R(F/S)) are measured at a specific incident angle (oblique incidence) and a ratio of these reflectance spectrums are determined (relative reflectance: R(F/S)/R(S)), a curve is obtained where the minimum and maximum values are adjacent due to the effect described in paragraph [0039]. This manner is shown in FIGS. 6(a) and 6(b). In this calculation, the substrate is silicon (ns=3.4155+i0.001 and ds=700 μm) and the thin film is silicon thermal oxide film (nf=1.812+i0.001 and df=20 μm). In FIG. 6(a), an absolute reflection spectrum of the on-substrate thin film (solid line) and a substrate absolute reflection spectrum of the substrate (dotted line), at an incident angle of 0, 70 and 85 degrees, are shown. FIG. 6(b) is a ratio of a spectrum at the solid line to a spectrum at the dotted line, for each of the angles. In the figure, the coordinate is logarithmically graduated. The relative reflection spectrum has a minimum value nearly coincident with a valley of the reflection spectrum of the on-substrate thin film while the relative reflection spectrum has a maximum value nearly coincident with a valley of the reflection spectrum of the substrate. Consequently, even in a case where the incident angle is changed, the spacing of between the minimum and maximum values is nearly constant at 0.2 GHz. Furthermore, the minimum and maximum values are nearly constant in height, i.e. 10,000%. These results are greatly different from those of the relative transmission spectrum described in paragraph [0032] and FIGS. 4(a) and 4(b). In this calculation, calculation has been made by taking k=0.001 instead of giving zero to the extinction coefficients (k) of both the substrate and the thin film. This is because, as described in paragraph [0037], the reflectivity valley becomes 0% at k=0 so that, in case a relative reflectance is calculated, spectral divergence occurs at the substrate-reflectance-valley frequency. k=0.001 was provided in order to avoid such a meaningless divergence.

When the substrate extinction coefficient k is a finite value greater than zero, the reflectance spectra of the substrate and the on-substrate thin film have valleys higher than 0%. However, the rises from 0% are equal in amount between both, and the ratio thereof, if determined, (see paragraph [0040]) is qualitatively equal to FIG. 6(b).

When the extinction coefficient k of the thin film is a finite value equal to or greater than zero, the reflectance spectra of the on-substrate thin film has a valley higher than that of the substrate wherein the reflectance spectrum of the substrate does not undergo a change. As a result, in a case where a ratio of the reflectance spectrum for the substrate and for the on-substrate thin film (relative reflectance is determined: R(F/S)/R(S)), the maximum value is nearly constant but the minimum value increases. The calculation result is shown in FIGS. 7(a) and 7(b). FIG. 7(a) is a relative reflectance spectrum in the case the extinction coefficient of the thin film is changed from k=0.001 to k=0.2 at an incident angle of 70 degrees. Although the maximum value is almost constant even in case k of the thin film is changed, the minimum value increases with increasing k. FIG. 7(b) is a plotting of the relationship between k and a minimum value. Although the minimum value increases with increasing k, it can be seen that the increase does not substantially rely upon the incident angle.

It can be seen that the relative reflectance spectrum increases as the distance between the maximum and minimum values of the refractive index of the thin film increases, from (Equation 6). The calculation result is shown in FIGS. 8(a) and 8(b). FIG. 8(a) is a relative reflectance spectrum in the case the refractive index of the thin film is changed from n=1.112 to n=3.4155 at an incident angle of 70 degrees. As n is increased, the minimum value shifts towards a lower frequency, though the maximum value does not change position. FIG. 8(b) is a plot of the frequency between maximum and minimum values regarding n of the thin film, wherein the frequency increases with increasing n but does not substantially rely upon the incident angle.

It can be seen that the influence, of a thin-film thickness change upon a relative-reflectance spectrum form, is nearly the same as the case where the thin-film refractive index is changed, from (Equation 6). The calculation result is shown in FIGS. 9(a) and 9(b). FIG. 9(a) is a relative reflectance spectrum in the case the thin-film thickness is changed from df=1 μm to 20 μm at an incident angle of 70 degrees. As df is increased, the minimum value shifts towards the lower frequency though the maximum value does not change position. FIG. 9(b) is a plot of the spacing between maximum and minimum values regarding df of the thin film. It can be seen that the spacing increases with increasing df but does not substantially rely upon incident angle.

[Effect of the Invention]

As described above, even where the thin film has a thickness of 1 μm or smaller, complex dielectric constant of the thin film on a substrate can be measured by an optical measurement without relying upon an electrical measurement.

BRIEF DESCRIPTION OF THE DRAWINGS

[FIGS. 1(a) to 1(d)] Transmittance spectrum for a substrate and a thin film on-substrate, in normal incidence.

FIG. 13(a) is a relative transmittance measurement result at an incident angle of 85 degrees in the case measuring point is changed on a sample surface of FIG. 13(b).

DESCRIPTION OF REFERENCE NUMERALS AND SIGNS

Figure 2:
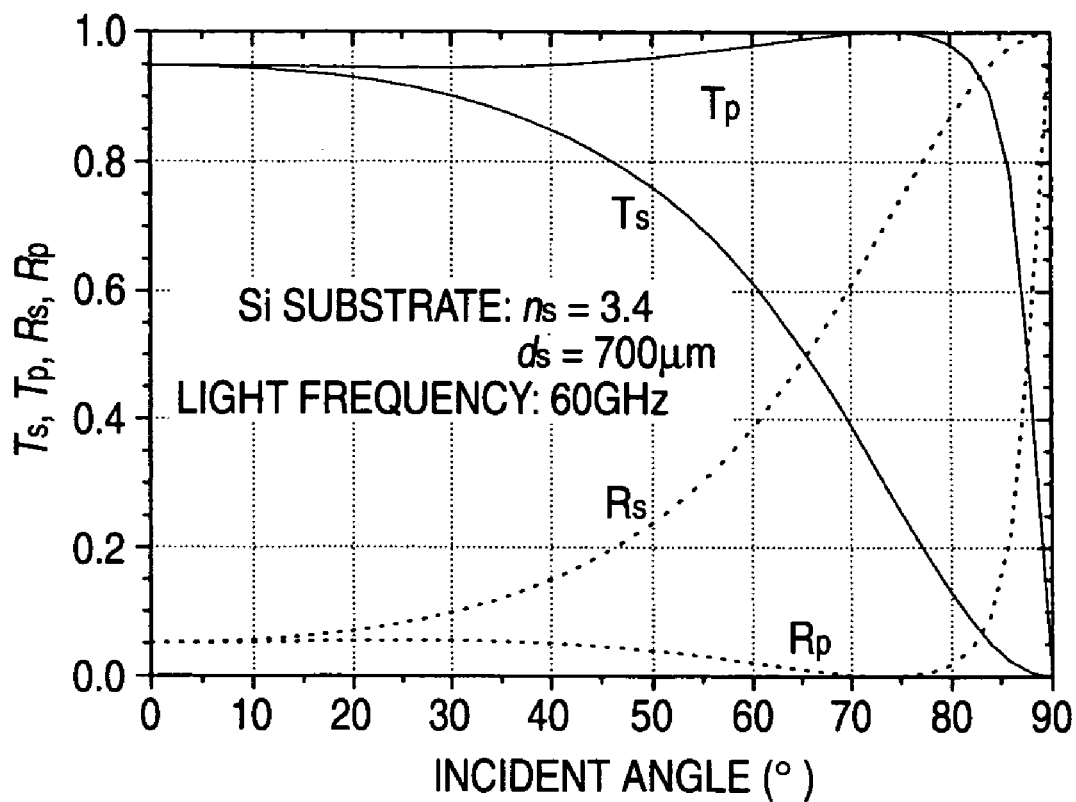
[FIG. 2] An on-incident-angle dependence of S and P polarization transmittance and reflectance, on incident angle.
Figure 3:
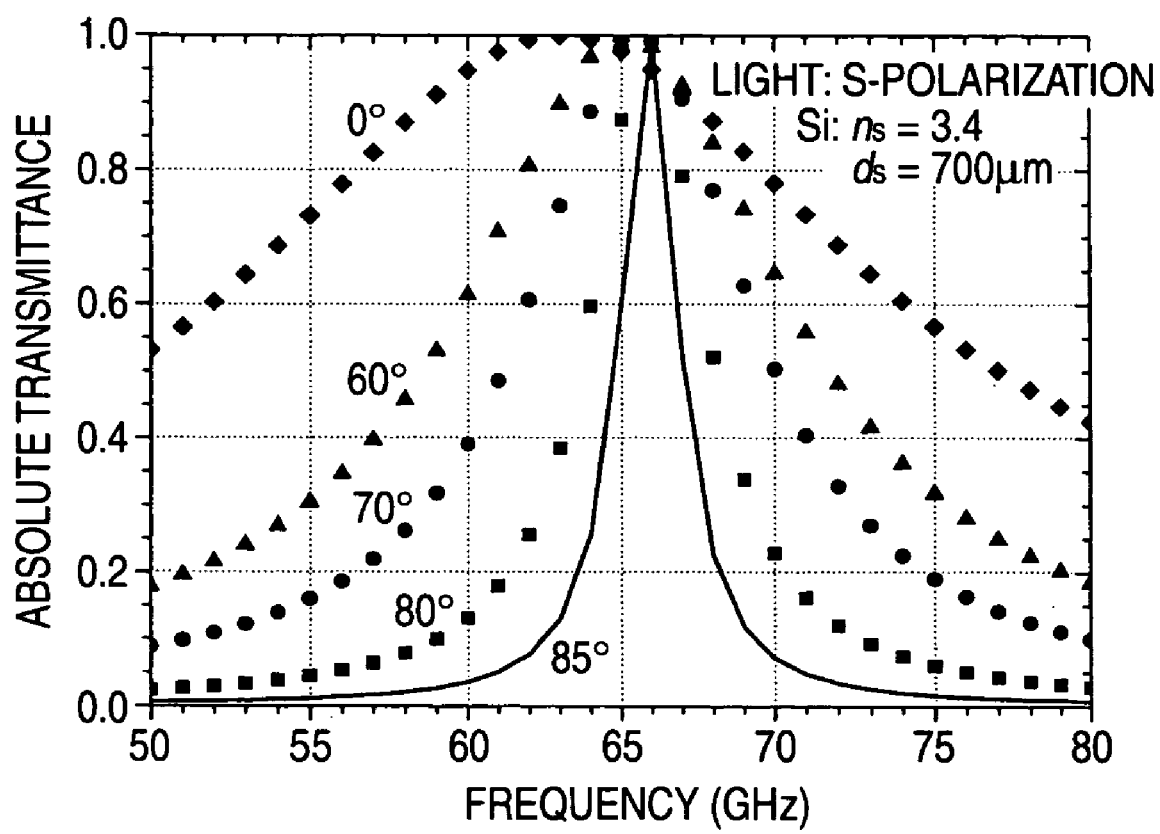
[FIG. 3] An S-polarization transmittance spectrum form in the case incident angle is changed.

10 Complex dielectric-constant measuring apparatus
11 Sample
12 Light source
13 Photodetector
14 Mechanical chopper
15, 17, 20, 22 Lens
16, 18, 19, 21 Aperture
23 polarizer and light-power attenuator
30 Incident system
31 Light-receiving system

BEST MODE FOR CARRYING OUT THE INVENTION

The best mode for carrying out the invention will be shown in the below.

Embodiment 1

<Embodiment Based on Light Transmission>

With reference to the figures, explanation is made on an embodiment of a complex-dielectric-constant measurement based on light transmission according to the invention.

Figure 10:
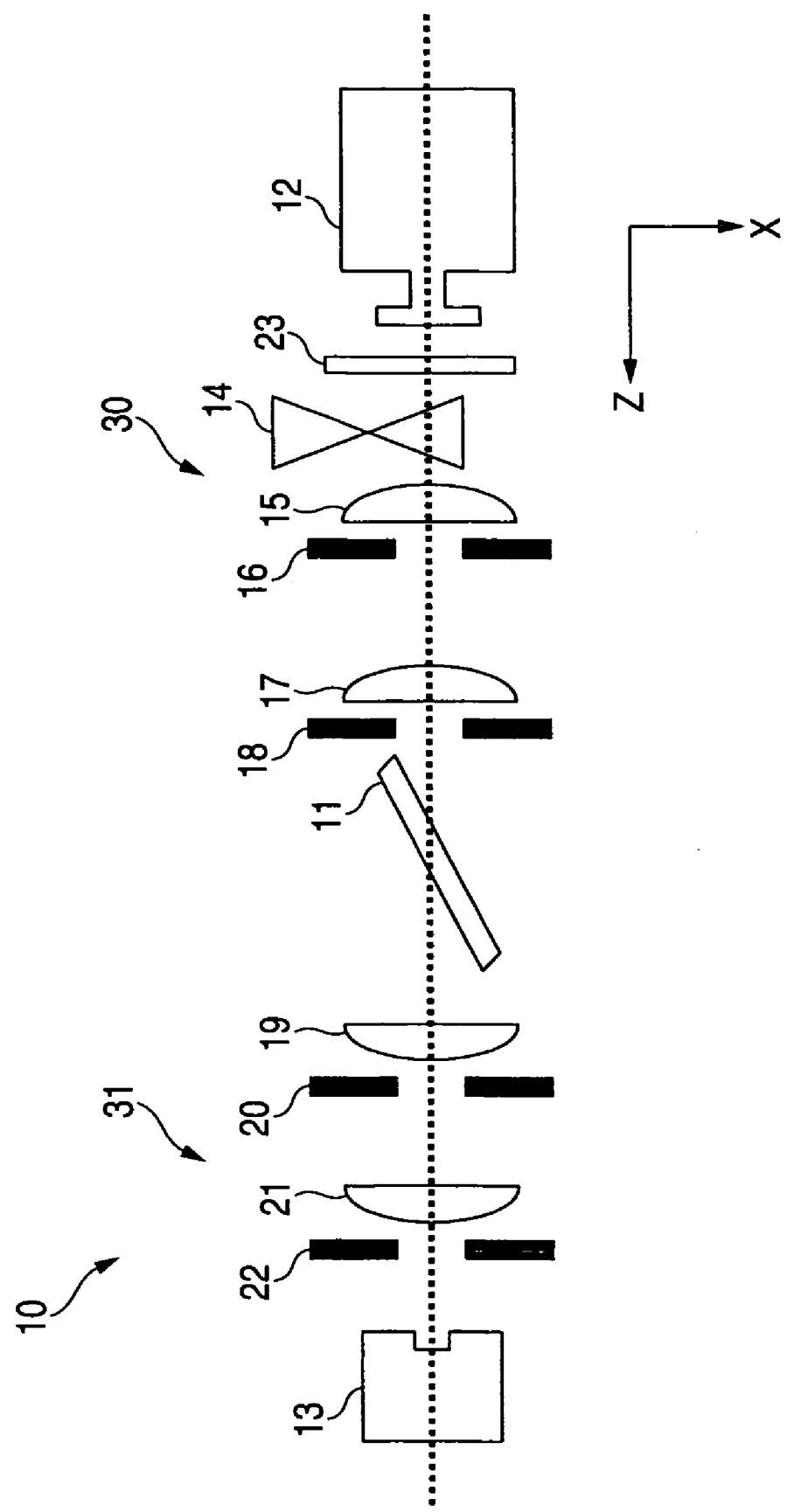
[FIG. 10] A concept view of a complex dielectric-constant measuring apparatus due to light transmission (embodiment 1).

FIG. 10 is a conceptual view of a complex-dielectric-constant measuring apparatus 10. The CW light exits a light source 12 (backward millimeter-wave tube (BWO), in the figure) and is intensity-modulated by a mechanical chopper 14. The light passes a lens 15, and an aperture 16 turns the light into a plane wave. In front of a sample 11, focusing is made onto a surface of the sample by a lens 17 and an aperture 18. A polarizer (not shown in the figure) and light-power attenuator (not shown in the figure) is inserted, as required, in the incident system 30. Only a part of the light is transmitted through the sample. This light is received by a lens 20 and an aperture 19 and changed into a plane wave. The light is received by a lens 22 and aperture 21 and collected onto a photodetector 13 (Golay Cell, in the figure). The intensity signal of the light is converted into an electric signal by the photodetector, and the electric signal is forwarded to a measuring instrument (not shown in the figure). The section of the apparatus from the sample to the photodetector is referred to as a light-receiving system 31. The light source, the sample, the photodetector, etc. are arranged nearly on a line. The propagating direction of the light is taken as z-axis. The light source is placed on an x-y auto stage (not shown in the figure) in order to desirably change the incident point upon the sample. The sample rests on an autorotation stage (not shown in the figure) in order to change the incident angle and is free to rotate about the vertical axis (y-axis). The photodetector is placed on an x-y-z auto stage (not shown in the figure) and an autorotation stage (not shown in the figure) so as to be set up at the optimal position. A sample holder (not shown in the figure) is devised so as not to block the incoming light even if entering obliquely. Furthermore, a radio-wave absorber (not shown in the figure) is attached on the sample holder in order to prevent the light that is not transmitted through the sample from entering the light-receiving system. When collimated light is incident upon the sample, the lenses 17, 20 are not used.

Figure 4:
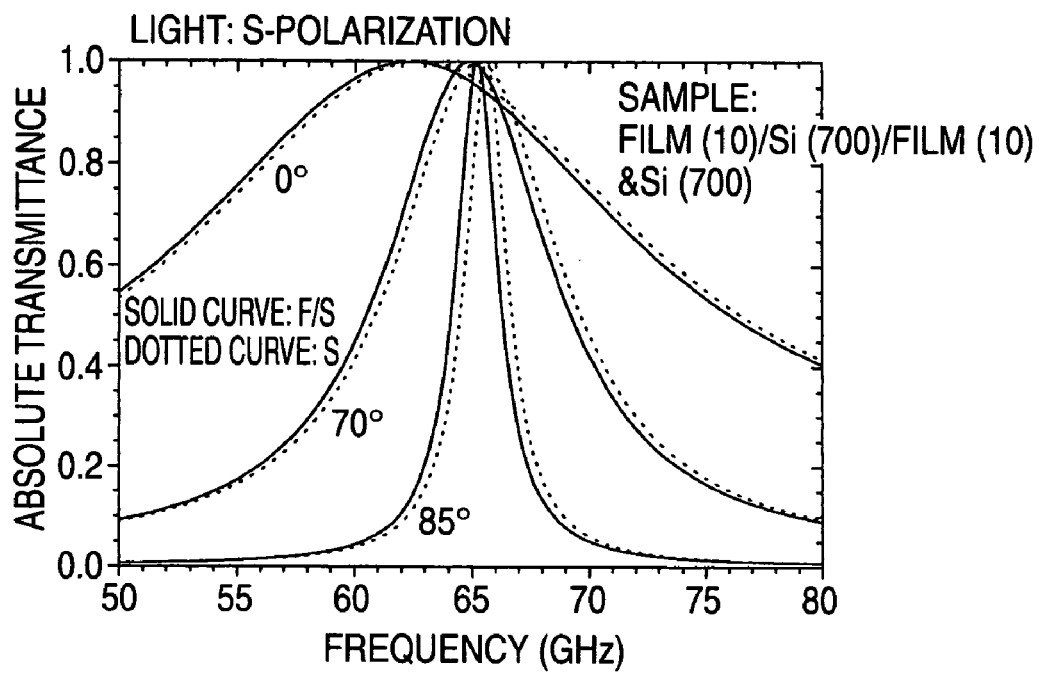
[FIGS. 4(a) and 4(b)] (a) An on-incident-angle dependence of absolute transmittance spectrum for a substrate and a thin film on the substrate, and (b) An on-incident-angle dependence of relative transmittance spectrum determined from those spectrums.
Figure 4:
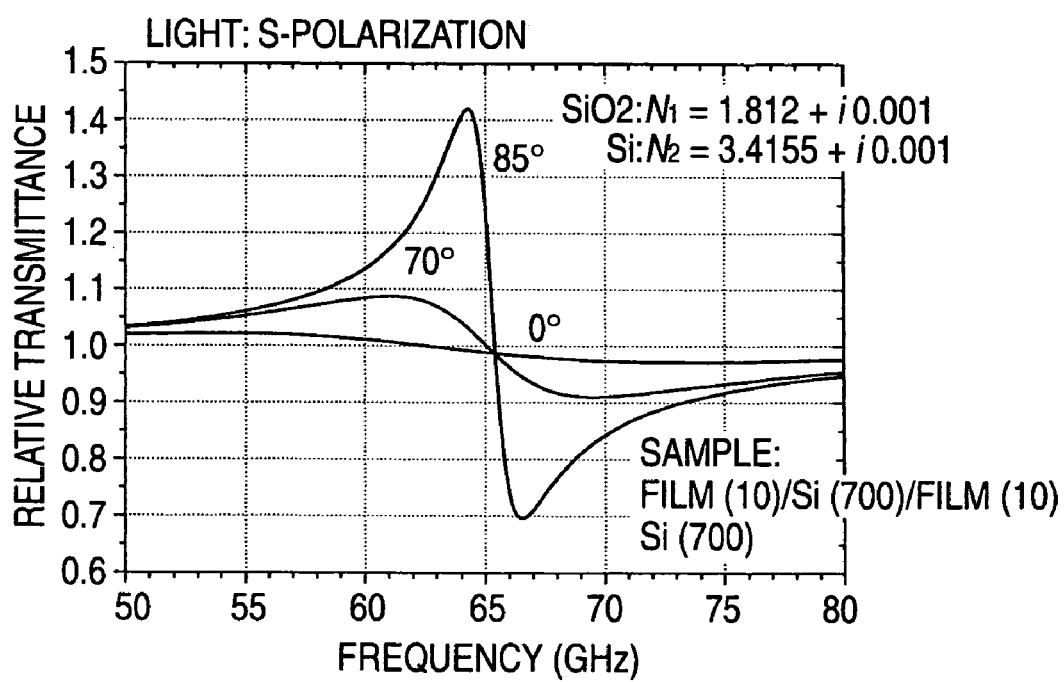
Figure 5:
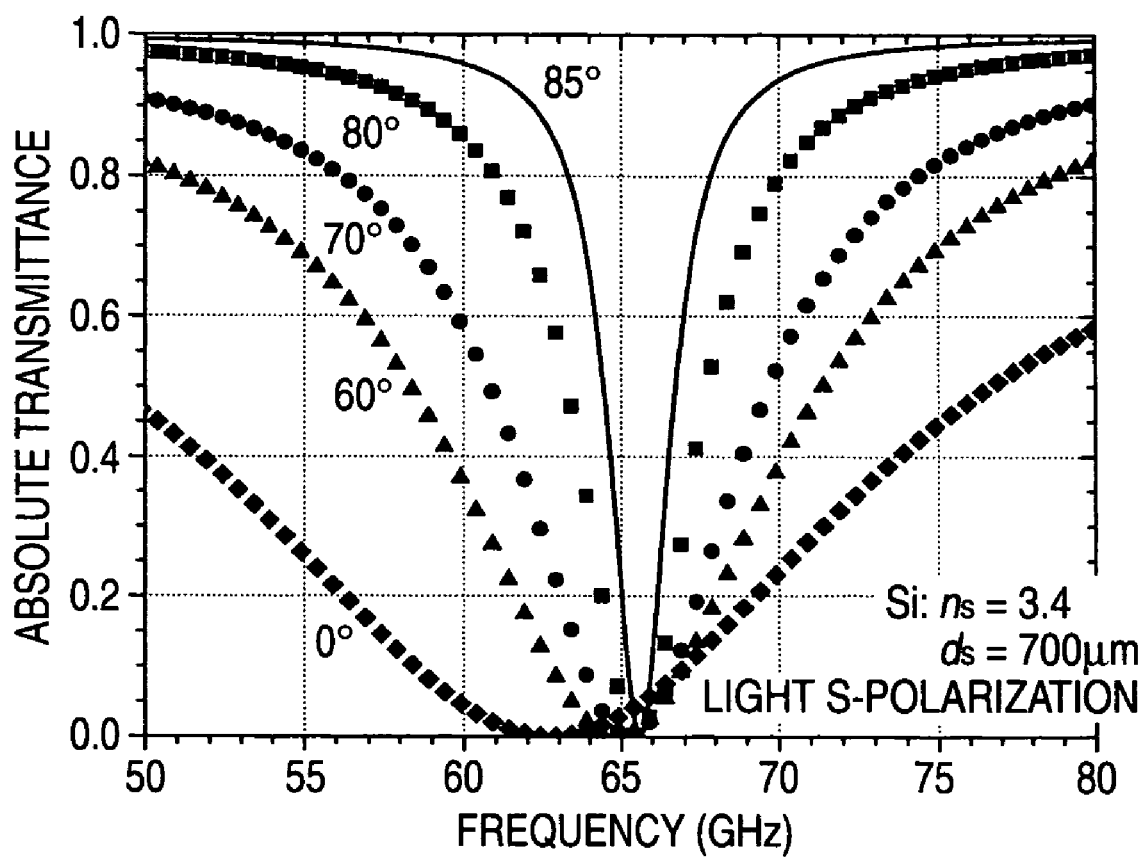
[FIG. 5] S-polarization reflectance spectrum form in the case incident angle is changed.
Figure 11:
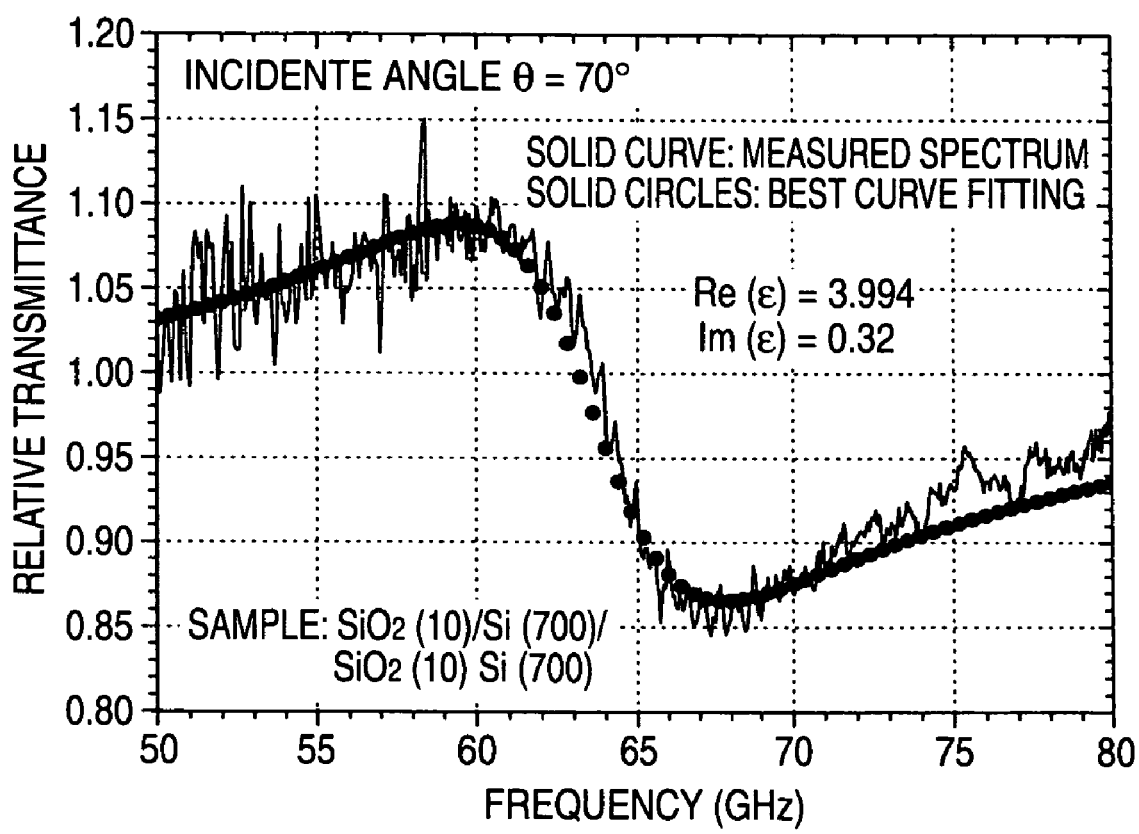
[FIG. 11] A drawing of a best fitting with a relative-transmittance measurement result in the case of S-polarization at an incidence of 70 degrees.

Ten-μm thick thermal oxide films ($SiO_2$) were formed on a main surface and a back surface of a silicon substrate having a diameter of 4 inches and a thickness of 700 μm. Then, the thermal oxide films, in the same positions on the main and back surfaces, were removed completely so that the oxide films on the main and the back surfaces have a semilunar form, thus preparing a sample exposed at its silicon surfaces. The sample was set up on the FIG. 10 sample holder. S-polarized light was irradiated obliquely (at an incident angle of 70 degrees) to the surface where the thermal oxide film remains (the upper half surface) and to the surface where is the oxide film was removed (the lower half surface), to measure transmission spectrums at each time. The transmission spectrums are referred to as $T(SiO_2/Si)$ and $T(Si)$, respectively. Here, a ratio of a transmission spectrum through the on-substrate-film sample to a transmission spectrum through the substrate was determined (relative transmittance=$T(SiO_2/Si)/T(Si)$). The result is shown by the solid line in FIG. 11. The "curve where the maximum and minimum values are adjacent" represented in the figure is qualitatively well matched to the FIG. 4(*b*) calculation result. Next, the equations, expressing a transmittance spectrum form provided by S-polarized light incident upon a (multi-layer) parallelepiped plate sample, are found in many books on optics (e.g. "Non-patent Document 4" in paragraph [0023]). With those equations, a transmittance spectrum for the substrate only ($Ts(Si)$) was calculated by using a silicon optical constant ($ns=3.4155$ and $ks=0$) and a substrate thickness ($ds=700$ μm). A transmittance spectrum for the sample formed by the substrate and the thin film ($Ts(SiO_2/Si)$) was best-fit to the FIG. 11 measurement result (solid line) by using a thin-film thickness ($df=20$ μm) and substrate optical constant while taking a thin-film optical constant as an unknown number ($nf$ and $kf$), the result of which is shown with solid circles in FIG. 11. The complex refractive index of the thin film thus determined is $nf=2.00$ and $kf=0.08$. From these, if using the paragraph [0011] relational expression, the complex dielectric constant of the $SiO_2$ thin film at 65 GHz is determined as $\in 1=3.994$ in its real part and $\in 2=0.32$ in its imaginary part.

Figure 12:
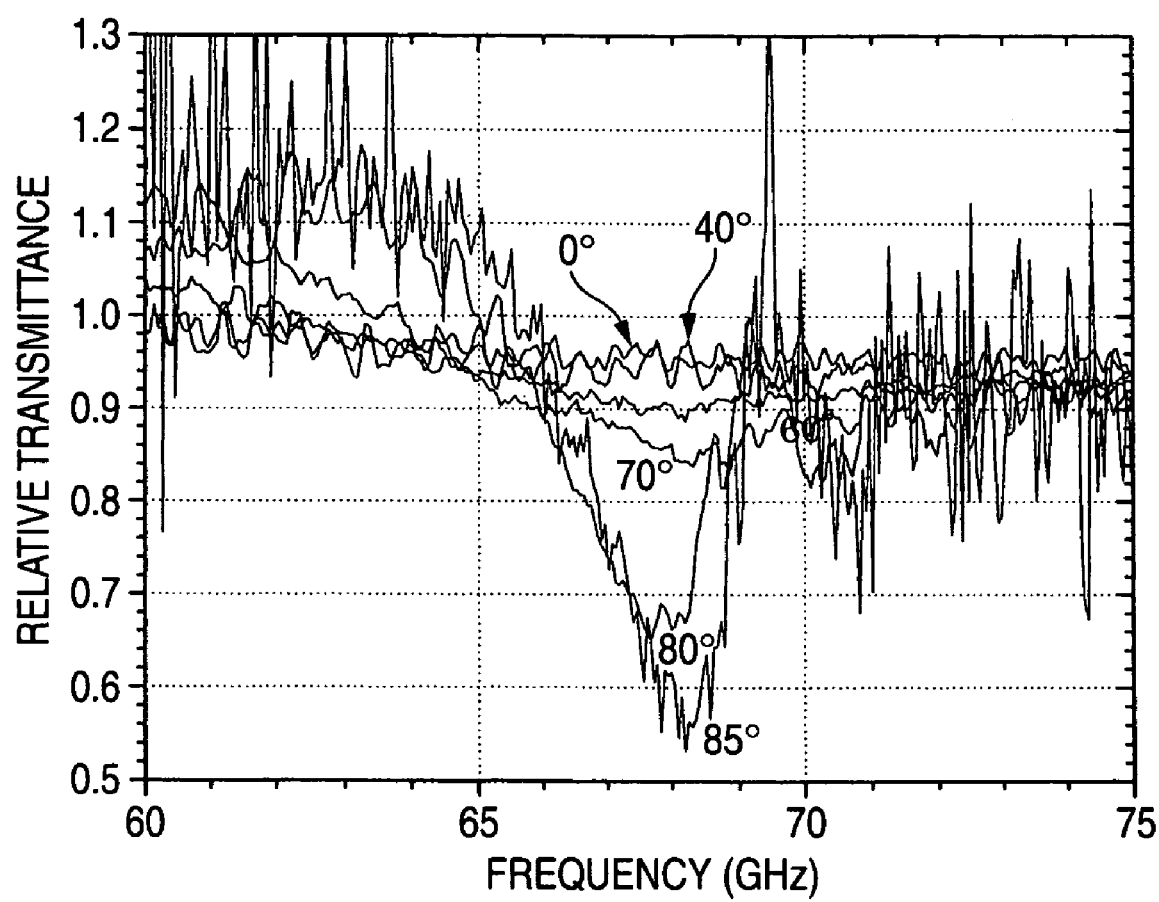
[FIG. 12] A drawing of a relative transmittance measurement result of S-polarization in the case incident angle is changed.

Using the same sample as in paragraph [0050], measurement was made at a changing incident angle. The result is shown in FIG. 12. In the measurement result, there is almost no difference in the relative transmittance at an incident angle of 0 to 40 degrees whereas there is a growth in the structure appearing in the relative transmittance as the incident angle is increased as 60, 70, 80 and 85 degrees. The dependence upon incident angle is also well matched to the FIG. 4(*b*) calculation result.

Figure 13:
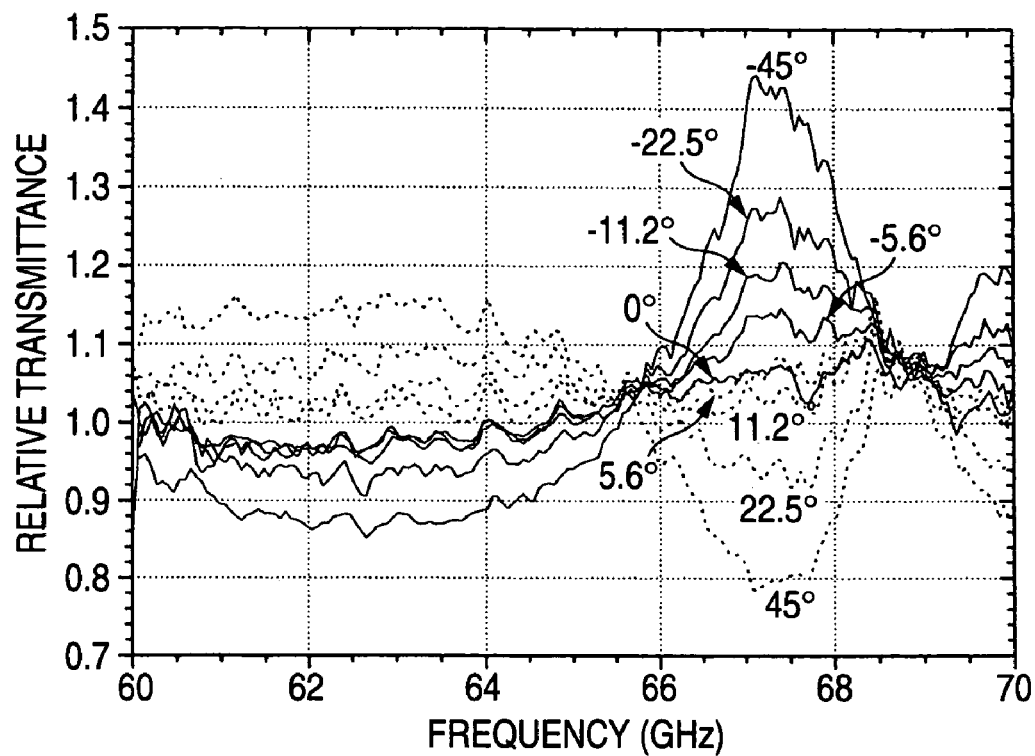
[FIGS. 13(a) and 13(b)]
Figure 13:
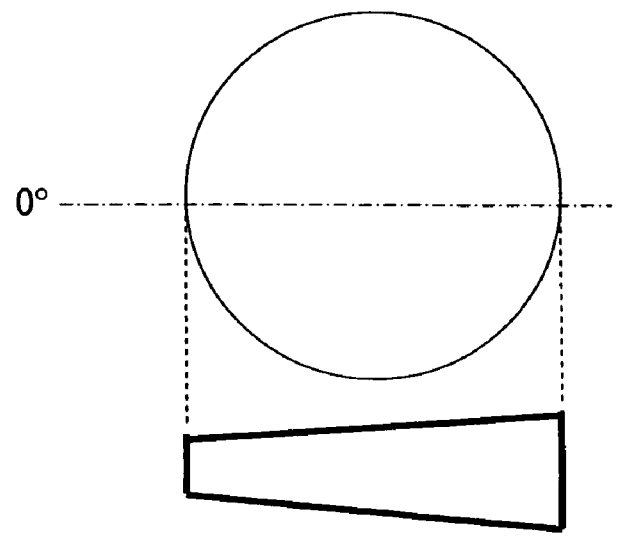

A silicon substrate having a uniform thickness 700 μm (bare substrate sample without forming a thin film) was put on the FIG. 10 sample holder, and an incident angle of the sample was set to 85 degrees. Then, while rotating the sample about the axis normal to the sample surface and passing the center thereof, a transmission spectrum through the sample upper half surface and a transmission spectrum through the sample lower half surface was made in order to calculate a ratio of those spectra (relative transmittance). The result is shown in FIG. 13(*a*). If the silicon wafer were a perfect parallelepiped plate, there could not be a structure where the maximum and minimum values are adjacent that is similar to FIG. 4(*b*). However, in FIG. 13(*a*), a structure appears where the maximum and minimum values are adjacent. In FIG. 13(*a*), the origin of sample rotation angle was selected as an angle at which the maximum and minimum values of relative transmittance spectrum have a height assuming a lowest curve (i.e. most flat curve). On the positive angle side, the relative transmittance spectrum is in a form similar to FIG. 4(*b*) wherein the minimum and maximum values increase in height as the angle increases toward 45 degrees. Meanwhile, the relative transmittance spectrum, on the negative angle side, is nearly in a mirror reflection of the positive-angle-side relative transmittance spectrum with respect to a relative transmittance spectrum at an angle of 0 degrees. From the measurement results, the commercially-available silicon wafers used today in the semiconductor industry are considered as "wedge-like disks" as typically shown in FIG. 13(*b*). The silicon wafer has a thickness deviation (difference in thickness between the maximum and the minimum) estimated to be 2 μm. In this manner, the "sample complex-dielectric-constant measuring apparatus based on optical spectral measurement" of the invention is capable of measuring the flatness of a sample as well.

Embodiment 2

<Embodiment Based on Light Reflection>

With reference to the figures, explanation is made with respect to an embodiment for measuring a complex dielectric constant based on light reflection according to the invention.

Figure 14:
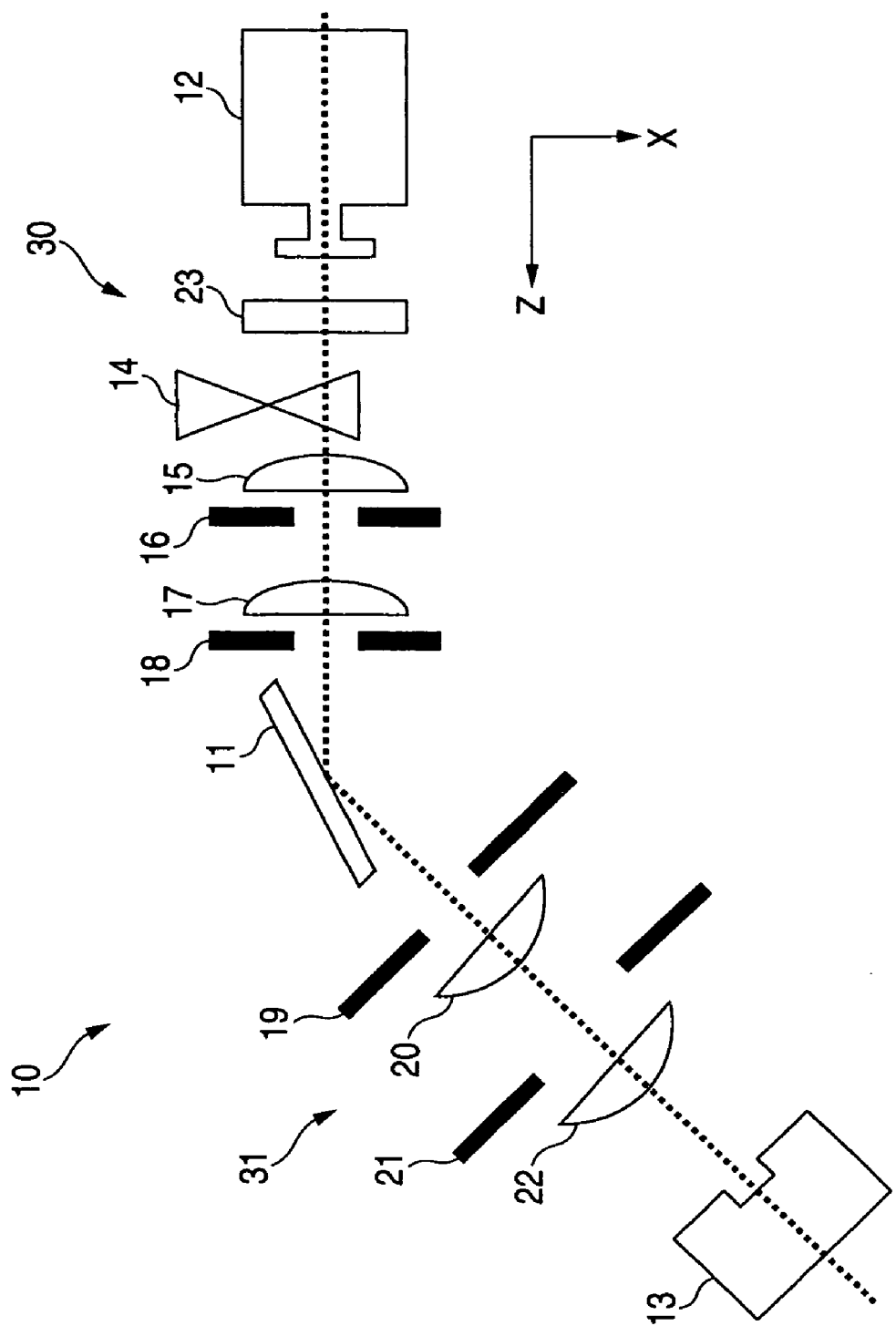
[FIG. 14] A concept view of a complex dielectric-constant measuring apparatus due to light reflection (embodiment 2).

FIG. 14 is a conceptual view of a complex-dielectric-constant measuring apparatus 10. The CW light exits a light source 12 and is intensity-modulated by a mechanical chopper 14. The light passes a lens 15, and an aperture 16 turns the light into a plane wave. In front of a sample 11, focusing is made onto a surface of the sample by a lens 17 and an aperture 18. A polarizer and light-power attenuator (23 in the figure) is inserted, as required, in the incident system 30. Only a part of the light is reflected by the sample. This light is received by a lens 20 and an aperture 19 and is changed into a plane wave. The light is received by an aperture 21 and a lens 22 and is collected onto a photodetector 13. The intensity signal of light the is converted into an electric signal by the photodetector. The electric signal is forwarded to a measuring instrument (not shown in the figure). The section of the measuring apparatus from the sample to the photodetector is referred to as a light-receiving system 31. The sample is rested upon an x-y auto stage (not shown in the figure) in order to desirably change the incident position of light upon the sample. Furthermore, the sample is placed on an autorotation stage (not shown in the figure) in order to change the incident angle. Thus, the sample is free to rotate about the vertical axis (y-axis). The photodetector is placed on an x-y-z auto stage (not shown in the figure) and an autorotation stage (not shown in the figure) so as to be set up in the optimal position. A sample holder (not shown in the figure) is devised so as not to block the incoming light even if entering obliquely. Furthermore, a radio-wave absorber (not shown in the figure) is attached on the sample holder in order to prevent the light reflected upon the sample holder from entering the light-receiving system. When collimated light is incident upon the sample, the lenses 17, 20 are not used.

Figure 6:
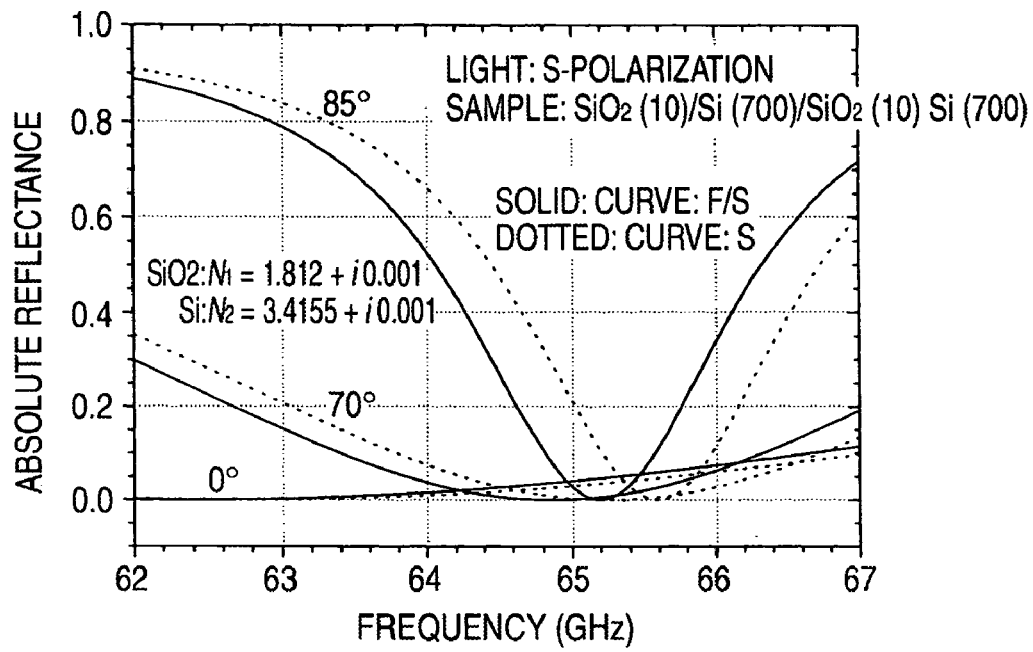
[FIGS. 6(a) and 6(b)] FIG. 6(a) A dependence of absolute reflectance spectrum for a substrate and on-substrate thin film upon incident angle, and FIG. 6(b) A dependence of relative reflectance spectrum determined from those spectrums upon incident angle.
Figure 6:
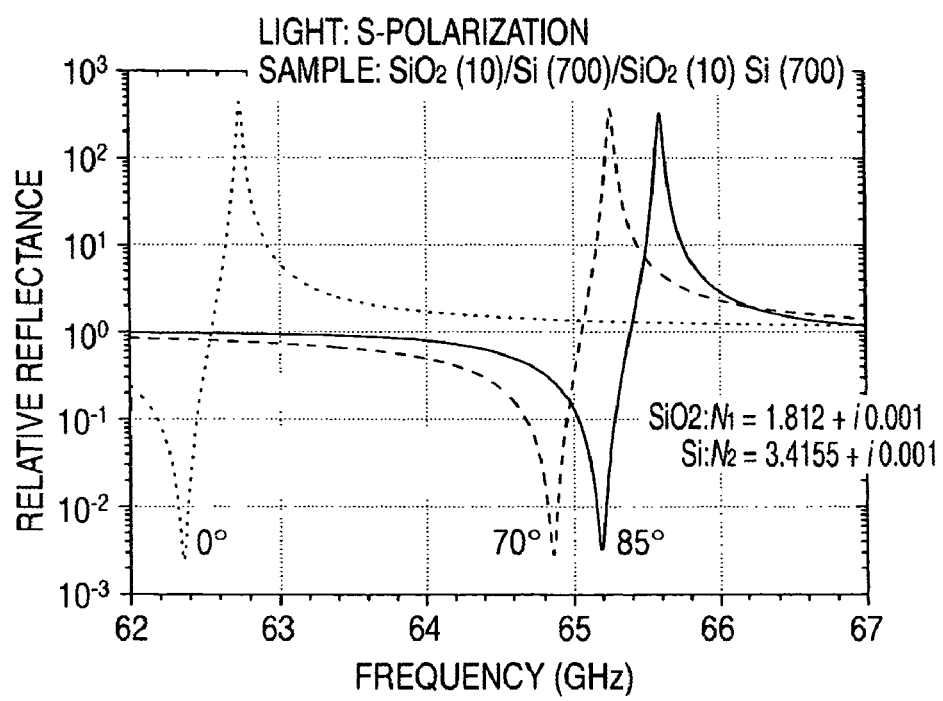
Figure 15:
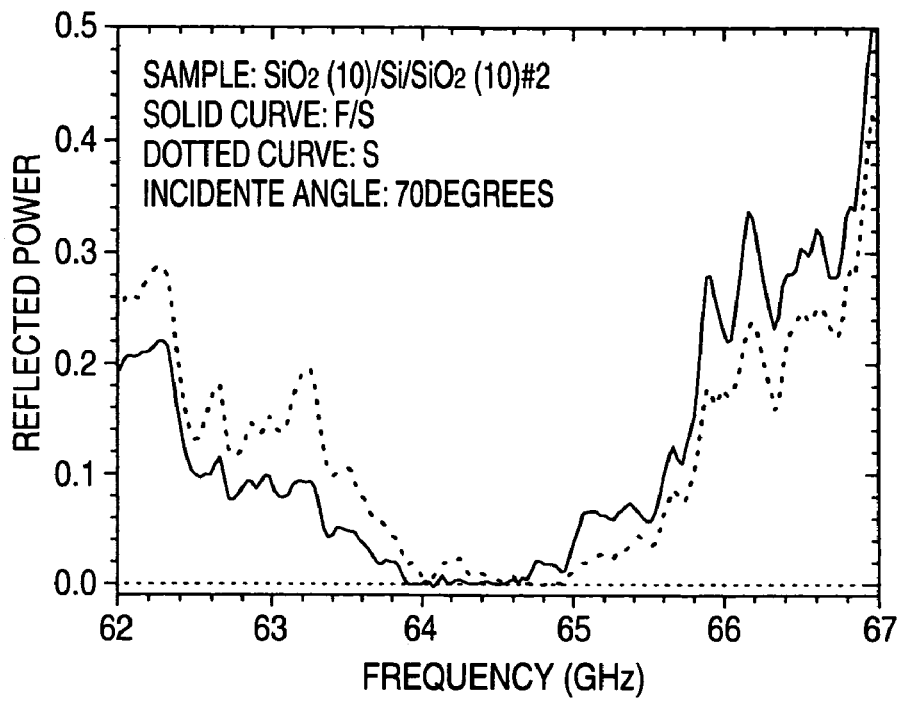
[FIGS. 15(a) and 15(b)] FIG. 15(a) A figure showing a reflection power at an incident angle of 70 degrees, by a 700-μm thick silicon substrate and a 20-μm thick $SiO_2$ film on the substrate, and FIG. 15 (b) a figure showing a relative reflection spectrum for the above spectrum.
Figure 15:
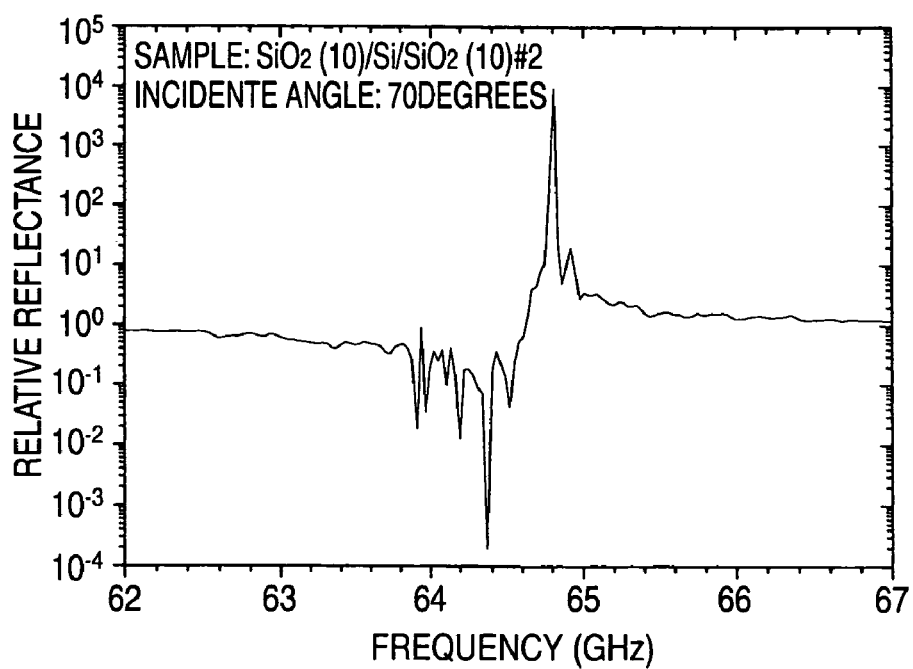

Ten-μm thick thermal oxide films ($SiO_2$) were formed on a main surface and a back surface of a silicon substrate having a diameter of 4 inches and a thickness of 700 μm. Then, the thermal oxide films, in the same positions on the main and back surfaces, were removed so that the oxide films on the main and the back surfaces have a semilunar form, thus preparing a sample exposed at its silicon surfaces. The sample was put on the FIG. 14 sample holder. S-polarized light was irradiated obliquely (at an incident angle of 70 degrees) to the surface where the thermal oxide film remains (the upper half surface) and to the surface where the oxide film was removed (the lower half surface), to measure reflection power at that time. The reflection powers are referred to as R(SiO$_2$/Si) and R(Si), respectively. The measurement result is shown in FIG. 15($a$). In this figure, the solid line represents R(SiO$_2$/Si) while the dotted line represents R(Si). Both curves have minimum values at around 65 GHz. Although the dotted line is greater than the solid line at a lower frequency than 65 GHz, the relationship in magnitude is inverted at a higher frequency than 65 GHz. This result is well matched to the FIG. 6($a$). Next, a ratio of a reflection spectrum upon the a thin film on the substrate (R(SiO$_2$/Si)) sample to a reflection spectrum upon substrate (R(Si)) sample was determined. (i.e., relative reflectance=R(SiO$_2$/Si)/R(Si)). The result is shown in FIG. 15($b$). The "curve where the maximum and minimum values are adjacent" represented in the figure is qualitatively well matched to the FIG. 6($b$) calculation result.

Figure 7:
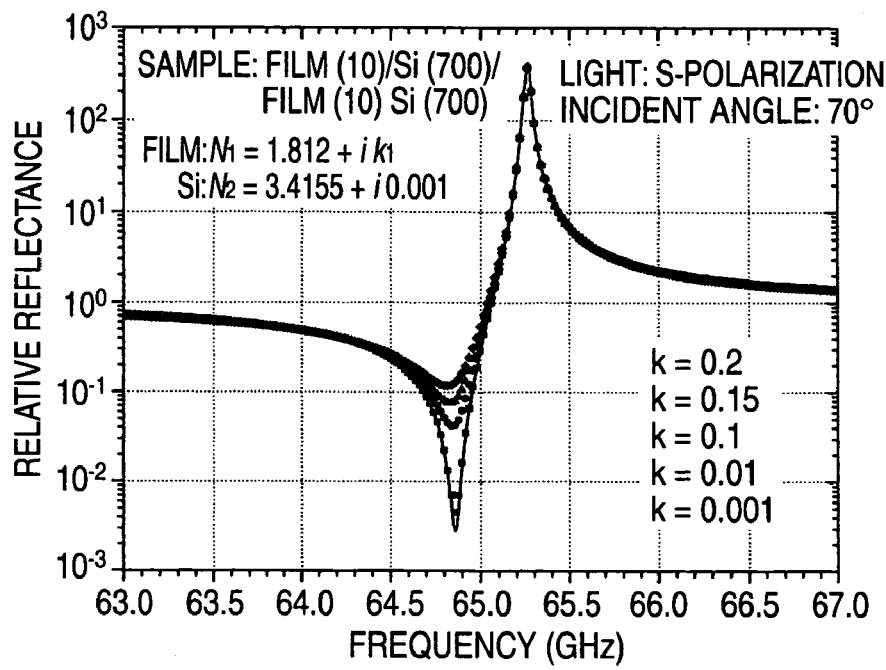
[FIGS. 7(a) and 7(b)] FIG. 7(a) A dependence of a relative reflectance spectrum for a substrate and on-substrate thin film upon a thin-film extinction coefficient, and FIG. 7(b) A plotting of a spectrum minimum value determined from those spectra, regarding a distinction coefficient.
Figure 7:
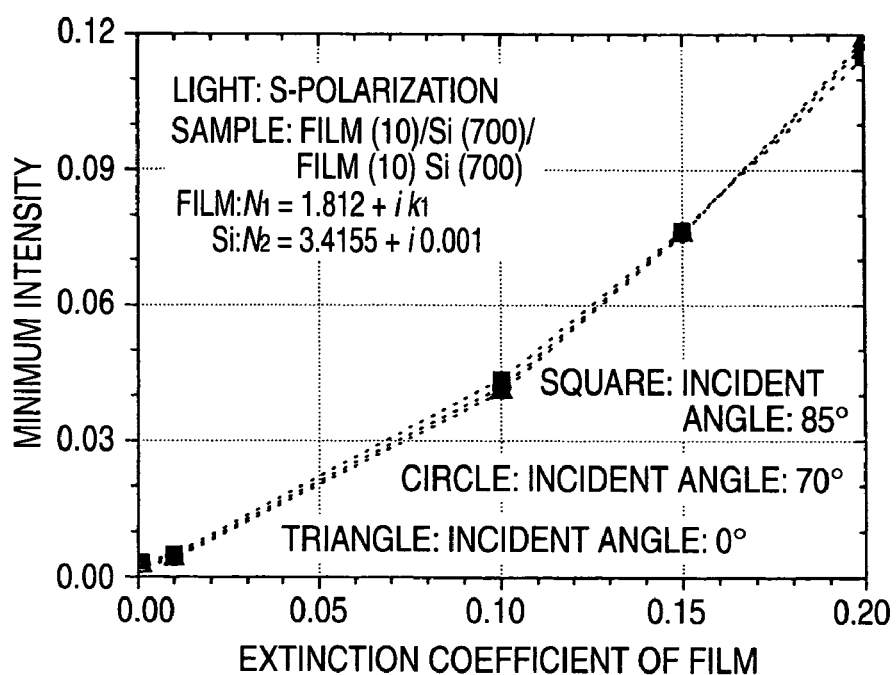
Figure 8:
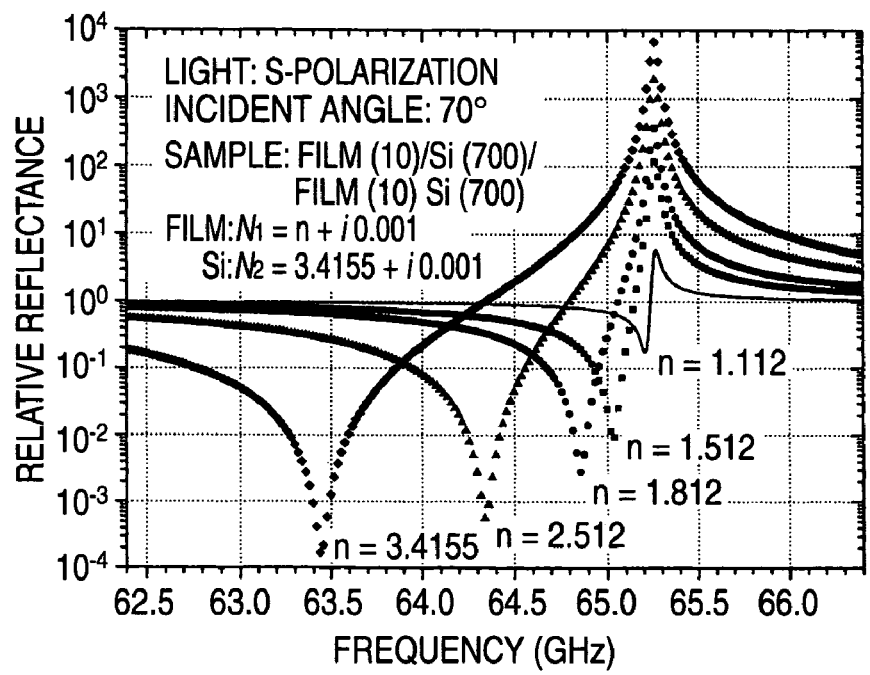
[FIGS. 8(a) and 8(b)] FIG. 8(a) A dependence of a relative reflectance spectrum of a substrate and a thin film on the substrate upon a thin-film refractive index, and FIG. 8(b) A plotting of a spacing of between the spectrum maximum and minimum values determined from those spectra, regarding a refractive index.
Figure 8:
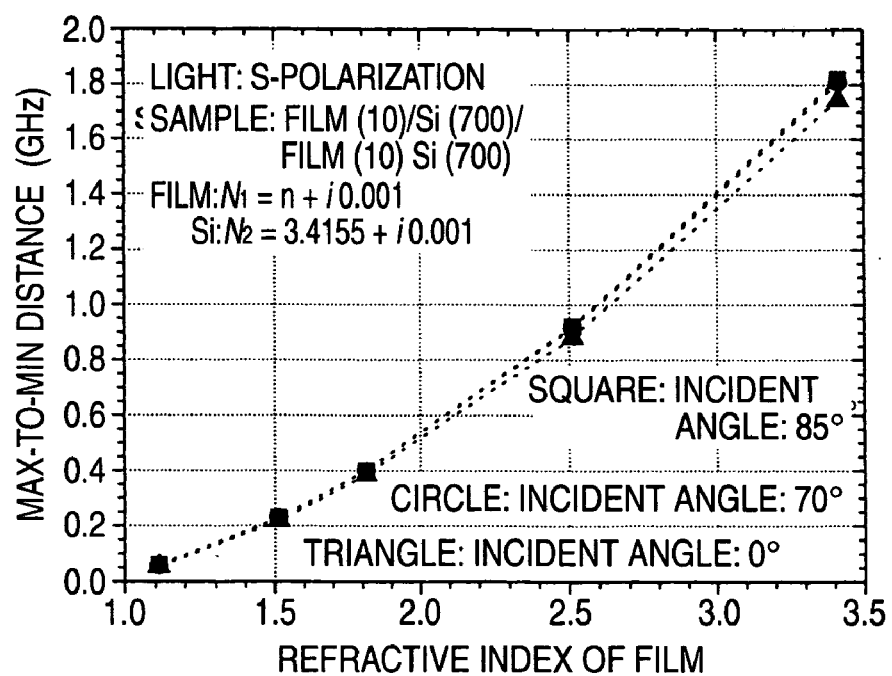
Figure 9:
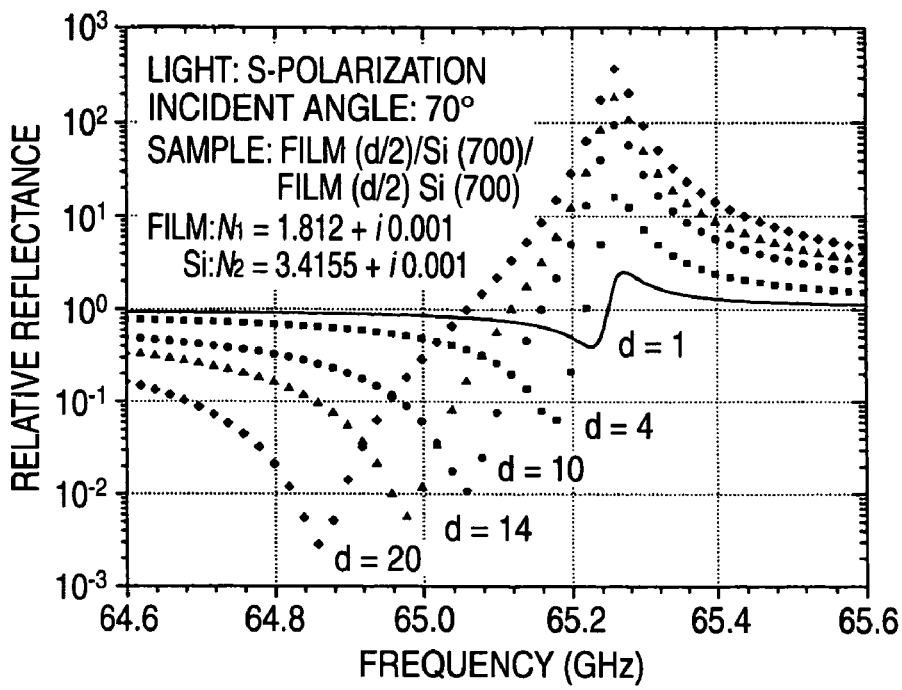
[FIGS. 9(a) and 9(b)] FIG. 9(a) A dependence of a relative reflectance spectrum for a substrate and a thin film on the substrate upon a thin-film thickness, and FIG. 9(b) Plotting of a spacing of between the spectrum maximum and minimum values determined from those spectrums, relative to a thin-film thickness.
Figure 9:
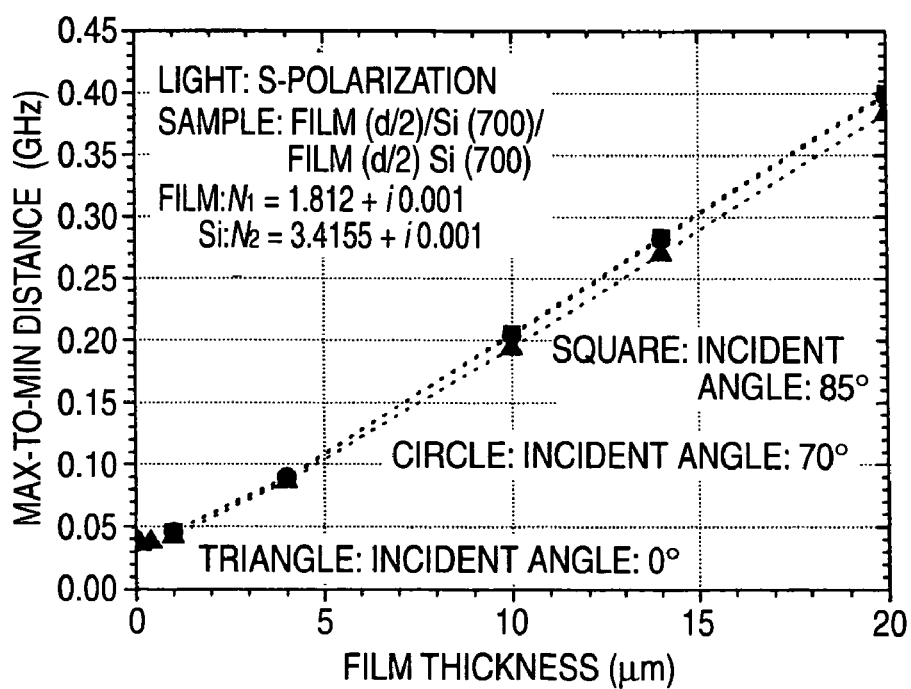

Description is made of a method to determine a complex dielectric constant from the measurement result FIGS. 15($a$) and 15($b$). Firstly, in FIG. 15($a$), the reflection power upon the sample having the on-substrate (Si) thermal oxide film (SiO$_2$) is equal in valley value to the reflection power upon the sample having only the substrate (Si). From the result, paragraph [0042] and FIG. 7($a$), the thin film can be estimated having an extinction coefficient of zero (k=0). Then, from FIG. 15($b$), the "distance between the minimum and maximum values" was determined to be 0.5 GHz. Because valley frequency, substrate thickness, substrate refractive index, incident angle and thin-film thickness are known in (Equation 6), the thin film is determined having a refractive index (nf) of nf=1.3. From the relationship between these results and paragraph [0011], the SiO$_2$ thin film is determined having a complex dielectric constant having ∈1=1.69 in its real part and ∈2=0 in its imaginary part.

The invention claimed is:

1. A method for measuring a dielectric constant of a thin film sample, comprising:
    irradiating the thin film sample with light at a first incident angle, whereby the light undergoes multiple internal reflections within the thin film sample;
    measuring light that has transmitted through or reflected on the thin film sample following said multiple internal reflections; and
    taking a ratio of a transmission spectrum or reflection spectrum through or upon a combination of the thin film and a substrate to a transmission spectrum or reflection spectrum through or upon the substrate only as a relative transmittance or relative reflectance, respectively;
    determining the relative transmittance or relative reflectance with respect to frequency over a range of frequencies;
    determining a complex dielectric constant of the thin film sample based upon the relative transmittance or relative reflectance with respect to frequency over a range of frequencies.

2. The method according to claim 1, wherein a complex dielectric constant of the thin film sample is determined by setting an incident angle of the incident light upon the thin film sample at 60 degrees or greater and smaller than 90 degrees.

3. The method according to claim 2, wherein the irradiation light has a wavelength in a region of a millimeter wave, a sub-millimeter wave or a tera-hertz frequency range of light.

4. The method according to claim 1, wherein the irradiation light is S-polarized light.

5. The method according to claim 1, wherein the irradiation light has a wavelength in a region of a millimeter wave, a sub-millimeter waive or a tera-hertz frequency range of light.

6. An apparatus for measuring a complex dielectric constant of a thin film sample by irradiating the sample with light, comprising:
    light irradiating unit that irradiates the thin film sample with light at a first incident angle, whereby the light undergoes multiple internal reflections within the thin film sample;
    measuring unit that measures light transmitted through or reflected upon the thin film sample following said multiple internal reflections; and
    determining unit that takes a ratio of a transmission spectrum or reflection spectrum through or upon a combination of the thin film and a substrate to a transmission spectrum or reflection spectrum through or upon the substrate only as a relative transmittance or relative reflectance, respectively,
    determines the relative transmittance or relative reflectance with respect to frequency over a range of frequencies, and
    determines a complex dielectric constant of the thin film sample based upon the relative transmittance or relative reflectance with respect to frequency over a range of frequencies.

7. The apparatus according to claim 6, wherein incident light upon the thin film sample is changeable in the position, and a photodetector for receiving the transmitted or reflected light is also changeable in the position.

8. The apparatus according to claim 7, wherein incident light upon the thin film sample is changeable in incident angle.

9. The apparatus according to claim 6, wherein incident light upon the thin film sample is changeable in incident angle.

* * * * *